United States Patent
Schwartz et al.

(10) Patent No.: US 11,071,482 B2
(45) Date of Patent: Jul. 27, 2021

(54) LANCET DEVICE WITH DEPTH ADJUSTMENT AND LANCET REMOVAL SYSTEM AND METHOD

(71) Applicant: STAT MEDICAL DEVICES, INC., N. Miami Beach, FL (US)

(72) Inventors: Brian Schwartz, Lake in the Hills, IL (US); Erik J. Moses, Carol Stream, IL (US); Mykola Pochyhaylo, Lviv (UA); Steven Schraga, Surfside, FL (US)

(73) Assignee: STAT MEDICAL DEVICES, INC., North Miami Beach, FL (US)

( * ) Notice: Subject to any disclaimer, the term of this patent is extended or adjusted under 35 U.S.C. 154(b) by 246 days.

(21) Appl. No.: 16/043,685

(22) Filed: Jul. 24, 2018

(65) Prior Publication Data

US 2018/0325438 A1 Nov. 15, 2018

Related U.S. Application Data

(62) Division of application No. 14/748,768, filed on Jun. 24, 2015, now Pat. No. 10,070,811.
(Continued)

(51) Int. Cl.
*A61B 5/15* (2006.01)
*A61B 5/151* (2006.01)

(52) U.S. Cl.
CPC ........ *A61B 5/15019* (2013.01); *A61B 5/1519* (2013.01); *A61B 5/150022* (2013.01);
(Continued)

(58) Field of Classification Search
None
See application file for complete search history.

(56) References Cited

U.S. PATENT DOCUMENTS

| 676,678 A | 6/1901 | Ellifrits |
| 1,135,465 A | 4/1915 | Pollock |

(Continued)

FOREIGN PATENT DOCUMENTS

| CA | 523 078 A | 3/1956 |
| EP | 0 061 102 A2 | 9/1982 |

(Continued)

OTHER PUBLICATIONS

Sutor et al., "Bleeding from Standardized Skin Punctures: Automated Technic for Recording Time, Intensity, and Pattern of Bleeding", A.J.C.P., vol. 55, pp. 541-549 (May 1971).

*Primary Examiner* — Thomas McEvoy
(74) *Attorney, Agent, or Firm* — Thomas | Horstemeyer, LLP

(57) ABSTRACT

A lancet device includes a housing, a removable front cap mounted to the housing, a lancet holding member, a trigger and an arming system comprising a grippable cocking member structured and arranged to place the lancet device in a trigger-set or armed position. A depth adjustment system includes a member that is at least slidable and partially rotatably mounted and that has an axis of rotation arranged substantially parallel to a center axis of the lancet holding member. An ejection system includes an ejector having a portion extending outside a sidewall opening of the housing and being located closer to a front end of the housing than to a rear end of the housing. The sidewall opening of the housing is arranged on an area of the housing located between the trigger and a wall of the housing located opposite the trigger. The ejection system is structured and arranged to at least one of prevent axial movement of the lancet holding member or remove or eject a lancet from the lancet holding member.

13 Claims, 44 Drawing Sheets

Related U.S. Application Data

(60) Provisional application No. 62/017,433, filed on Jun. 26, 2014.

(52) U.S. Cl.
CPC ...... *A61B 5/15113* (2013.01); *A61B 5/15117* (2013.01); *A61B 5/15128* (2013.01); *A61B 5/15194* (2013.01); *A61B 5/150259* (2013.01); *A61B 5/150412* (2013.01); *A61B 5/150503* (2013.01); *A61B 5/150824* (2013.01)

(56) References Cited

U.S. PATENT DOCUMENTS

| | | |
|---|---|---|
| 2,699,784 A | 1/1955 | Krayl |
| 2,823,677 A | 2/1958 | Hein, Jr. |
| 2,848,809 A | 8/1958 | Crowder |
| 3,030,959 A | 4/1962 | Grunert |
| 3,589,213 A | 6/1971 | Gourley |
| 3,760,809 A | 9/1973 | Campbell, Jr. |
| 4,064,871 A | 12/1977 | Reno |
| 4,139,011 A | 2/1979 | Benoit et al. |
| 4,157,086 A | 6/1979 | Malorama et al. |
| 4,203,446 A | 5/1980 | Hofert et al. |
| 4,257,561 A | 3/1981 | McKinney |
| 4,388,925 A | 6/1983 | Burns |
| 4,426,105 A | 1/1984 | Plaquin et al. |
| 4,438,770 A | 3/1984 | Unger et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,539,988 A | 9/1985 | Shirlet et al. |
| 4,553,541 A | 11/1985 | Burns |
| 4,628,929 A | 12/1986 | Integan et al. |
| 4,643,189 A | 2/1987 | Mintz |
| 4,785,858 A | 11/1988 | Valentini et al. |
| RE32,922 E | 5/1989 | Levin et al. |
| 4,834,667 A | 5/1989 | Fowler et al. |
| 4,858,607 A | 8/1989 | Jordan et al. |
| 4,869,249 A | 9/1989 | Crossman et al. |
| 4,895,147 A | 1/1990 | Bodicky et al. |
| 4,924,879 A | 5/1990 | O'Brien |
| 4,976,724 A | 12/1990 | Nieto et al. |
| 4,990,154 A | 2/1991 | Brown et al. |
| 5,035,704 A | 7/1991 | Lambert et al. |
| 5,074,872 A | 12/1991 | Brown et al. |
| 5,133,730 A | 7/1992 | Biro et al. |
| 5,147,375 A | 9/1992 | Sullivan et al. |
| 5,201,324 A | 4/1993 | Swierczek |
| 5,212,879 A | 5/1993 | Biro et al. |
| 5,269,799 A | 12/1993 | Daniel |
| 5,282,822 A | 2/1994 | Macors et al. |
| 5,304,193 A | 4/1994 | Zhadanov |
| 5,314,441 A | 5/1994 | Cassack et al. |
| 5,324,303 A | 6/1994 | Strong et al. |
| 5,318,584 A | 7/1994 | Lange et al. |
| 5,350,392 A | 9/1994 | Purcell et al. |
| 5,356,420 A | 10/1994 | Czernecki et al. |
| 5,366,470 A | 11/1994 | Ramel |
| 5,368,047 A | 11/1994 | Suzuki et al. |
| 5,395,388 A | 3/1995 | Schraga |
| 5,423,847 A | 6/1995 | Strong et al. |
| 5,439,473 A | 8/1995 | Jorgensen |
| 5,454,828 A | 10/1995 | Schraga |
| 5,464,418 A | 11/1995 | Schraga |
| 5,476,101 A | 12/1995 | Schramm et al. |
| 5,487,748 A | 1/1996 | Marshall |
| 5,509,345 A | 4/1996 | Crktich |
| 5,518,004 A | 5/1996 | Schraga |
| 5,527,333 A | 6/1996 | Nikkels et al. |
| 5,527,334 A | 6/1996 | Kanner et al. |
| 5,529,581 A | 6/1996 | Cusack |
| 5,545,174 A | 8/1996 | Schenk et al. |
| 5,554,166 A | 9/1996 | Lange et al. |
| 5,569,286 A | 10/1996 | Peckham et al. |
| 5,569,287 A | 10/1996 | Tezuka et al. |
| 5,571,132 A | 11/1996 | Mawhirt et al. |
| D376,203 S | 12/1996 | Schraga |
| 5,613,978 A | 3/1997 | Harding |
| 5,628,764 A | 3/1997 | Schraga |
| 5,628,765 A | 3/1997 | Morita |
| 5,643,306 A | 7/1997 | Schraga |
| 5,662,672 A | 9/1997 | Pambianchi et al. |
| 5,730,753 A | 3/1998 | Morita |
| 5,733,300 A | 3/1998 | Pambianchi et al. |
| 5,741,288 A | 4/1998 | Rife |
| RE35,803 E | 5/1998 | Lange Etal |
| 5,772,677 A | 6/1998 | Mawhirt et al. |
| 5,797,940 A | 8/1998 | Mawhirt et al. |
| 5,797,942 A | 8/1998 | Schraga |
| 5,873,887 A | 2/1999 | King et al. |
| 5,879,367 A | 3/1999 | Latterell et al. |
| 5,908,434 A | 6/1999 | Schraga |
| 5,916,230 A | 6/1999 | Brenneman et al. |
| 5,971,941 A | 10/1999 | Simons et al. |
| 5,984,940 A | 11/1999 | Davis et al. |
| 6,010,519 A | 1/2000 | Mawhirt et al. |
| 6,022,366 A | 2/2000 | Schraga |
| 6,042,595 A | 3/2000 | Morita |
| 6,045,567 A | 4/2000 | Taylor et al. |
| 6,056,765 A | 5/2000 | Bajaj et al. |
| 6,071,294 A | 6/2000 | Simons et al. |
| D428,150 S | 7/2000 | Ruf et al. |
| 6,086,545 A | 7/2000 | Roe et al. |
| 6,136,013 A | 10/2000 | Marshall et al. |
| 6,152,942 A | 11/2000 | Brenneman et al. |
| 6,156,050 A | 12/2000 | Davis et al. |
| 6,156,051 A | 12/2000 | Schraga |
| 6,161,976 A | 12/2000 | Liu |
| 6,168,606 B1 | 1/2001 | Levin et al. |
| 6,183,489 B1 | 2/2001 | Douglas et al. |
| 6,190,398 B1 | 2/2001 | Schraga |
| 6,192,891 B1 | 2/2001 | Gravel et al. |
| 6,197,040 B1 | 3/2001 | Levaughn et al. |
| 6,210,420 B1 | 4/2001 | Mauze et al. |
| 6,221,089 B1 | 4/2001 | Mawhirt |
| 6,228,100 B1 | 5/2001 | Schraga |
| 6,258,112 B1 | 7/2001 | Schraga |
| 6,283,982 B1 | 9/2001 | Levaughn et al. |
| 6,306,152 B1 | 10/2001 | Verdonk et al. |
| 6,322,574 B1 | 11/2001 | Lloyd et al. |
| 6,322,575 B1 | 11/2001 | Schraga |
| 6,332,871 B1 | 12/2001 | Douglas et al. |
| 6,346,114 B1 | 2/2002 | Schraga |
| 6,358,265 B1 | 3/2002 | Thorne, Jr. et al. |
| 6,364,889 B1 | 4/2002 | Kheiri et al. |
| 6,379,317 B1 | 4/2002 | Kintzig et al. |
| 6,395,495 B1 | 5/2002 | Montagnier et al. |
| 6,409,740 B1 | 6/2002 | Kuhr et al. |
| 6,419,661 B1 | 7/2002 | Kuhr et al. |
| 6,451,040 B1 | 9/2002 | Purcell |
| 6,464,649 B1 | 10/2002 | Duchon et al. |
| 6,506,168 B1 | 1/2003 | Fathallah et al. |
| 6,514,270 B1 | 2/2003 | Schrag A |
| 6,530,937 B1 | 3/2003 | Schraga |
| 6,540,762 B1 | 4/2003 | Bertling |
| 6,558,402 B1 | 5/2003 | Chelak et al. |
| 6,602,268 B2 | 8/2003 | Kuhr |
| 6,645,219 B2 | 11/2003 | Roe |
| 7,087,068 B1 | 8/2006 | Marshall et al. |
| 7,175,641 B1 | 2/2007 | Schraga |
| 7,299,081 B2 | 11/2007 | Mace et al. |
| 7,311,718 B2 | 12/2007 | Schraga |
| 2001/0027327 A1 | 10/2001 | Schraga |
| 2001/0039387 A1 | 11/2001 | Rutynowski et al. |
| 2002/0029058 A1 | 3/2002 | Levaughn |
| 2002/0040230 A1 | 4/2002 | Kuhr |
| 2002/0077650 A1 | 6/2002 | Schraga |
| 2003/0050627 A1 | 3/2003 | Taylor |
| 2003/0050655 A1 | 3/2003 | Roe |
| 2003/0050656 A1 | 3/2003 | Schraga |
| 2003/0083686 A1 | 5/2003 | Freeman et al. |
| 2004/0092995 A1 | 5/2004 | Boecker |

(56) References Cited

U.S. PATENT DOCUMENTS

| | | |
|---|---|---|
| 2004/0230216 A1 | 11/2004 | Levaughn et al. |
| 2004/0236362 A1 | 11/2004 | Schraga |
| 2005/0090850 A1 | 4/2005 | Thoes |
| 2005/0118071 A1 | 6/2005 | Sacherer |
| 2005/0234495 A1 | 10/2005 | Schraga |
| 2005/0288699 A1 | 12/2005 | Schraga |
| 2006/0173478 A1 | 8/2006 | Schraga |
| 2006/0200181 A1 | 9/2006 | Fukuzawa |
| 2006/0206135 A1 | 9/2006 | Uehata |
| 2006/0224172 A1 | 10/2006 | Levaughn et al. |
| 2006/0229652 A1 | 10/2006 | Iio et al. |
| 2006/0241668 A1 | 10/2006 | Schraga |
| 2006/0247670 A1 | 11/2006 | Levaughn |
| 2007/0083222 A1 | 4/2007 | Schraga |
| 2008/0033468 A1 | 2/2008 | Lathrop et al. |
| 2008/0039885 A1 | 2/2008 | Purcell |
| 2008/0195132 A1 | 8/2008 | Schraga |
| 2008/0195133 A1 | 8/2008 | Zhong |
| 2010/0274273 A1 | 10/2010 | Schraga |
| 2011/0160759 A1 | 6/2011 | Schraga |

FOREIGN PATENT DOCUMENTS

| | | |
|---|---|---|
| EP | 0 137 975 A2 | 4/1985 |
| EP | 0 189 117 A2 | 7/1986 |
| EP | 0 838 195 A1 | 4/1998 |
| EP | 0 885 590 A1 | 12/1998 |
| EP | 0 904 731 A2 | 3/1999 |
| EP | 1 074 219 A2 | 2/2001 |
| EP | 1 142 534 | 10/2001 |
| FR | 1 126 718 A | 11/1956 |
| FR | 2 797 579 A1 | 8/1999 |
| KR | 10-2001-0020623 A | 1/2000 |
| WO | 93/19671 A1 | 10/1993 |
| WO | 99/63897 A1 | 12/1999 |
| WO | 03/022130 A2 | 3/2003 |
| WO | 2005/018710 A2 | 3/2005 |
| WO | 2006/096630 | 9/2006 |

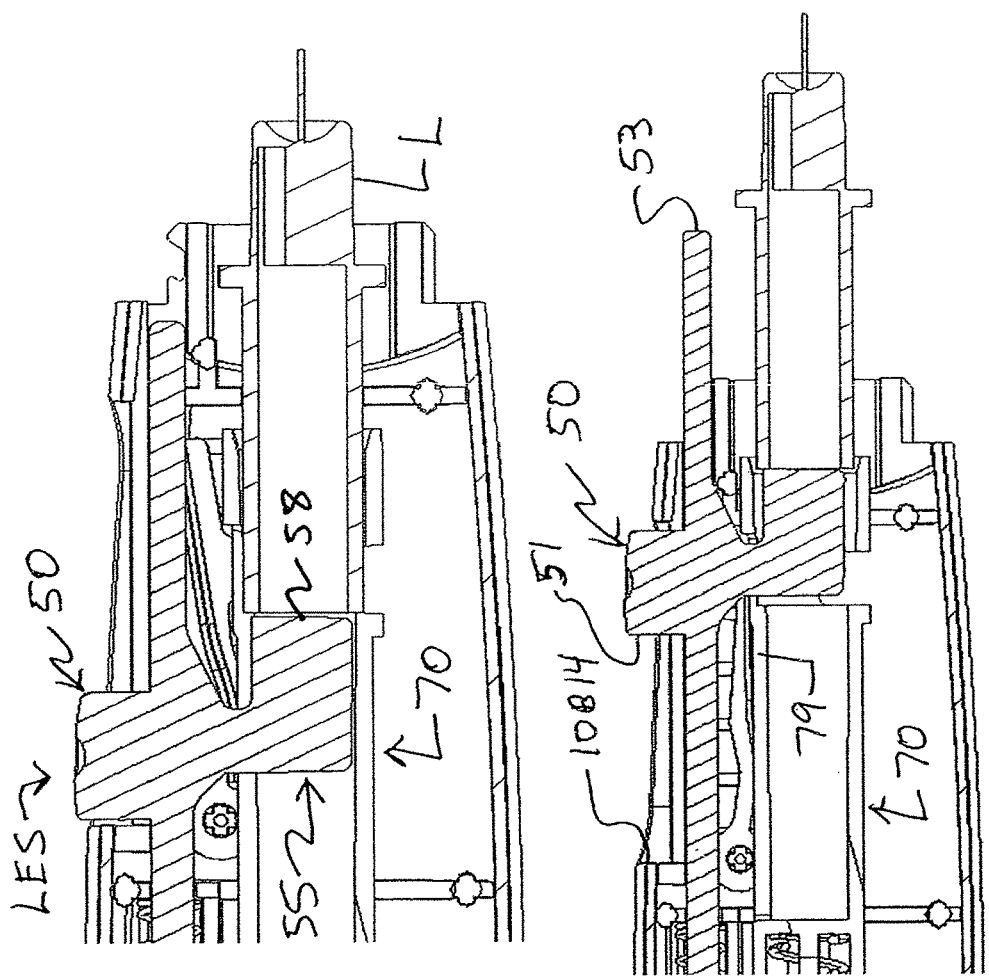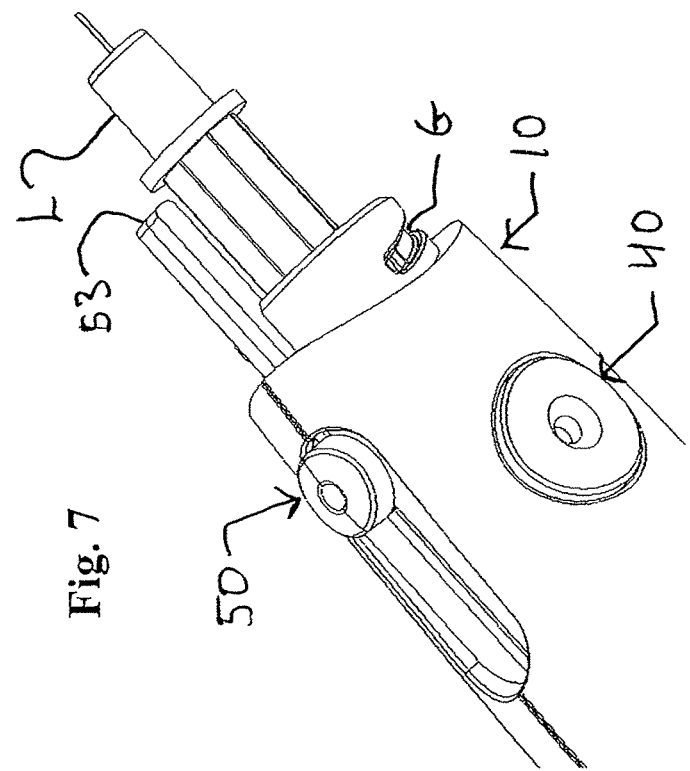

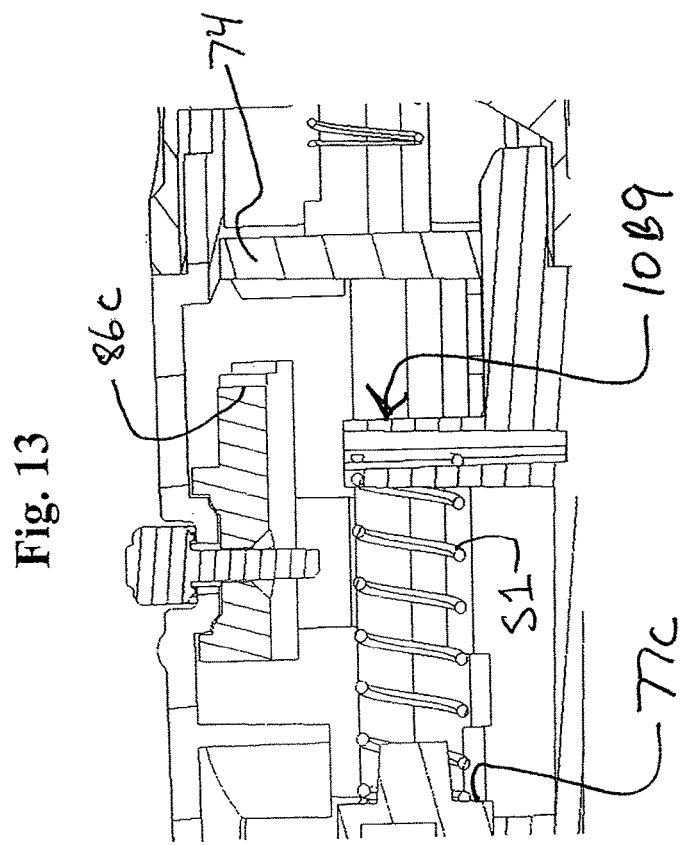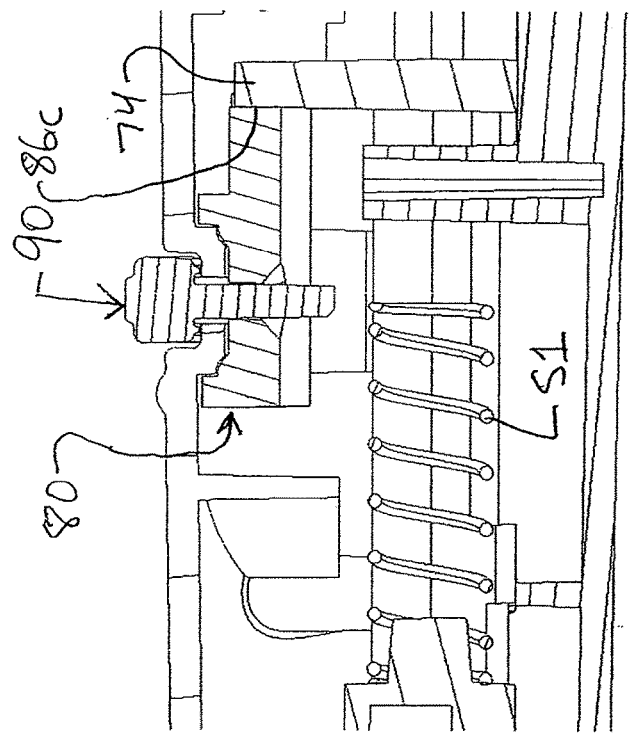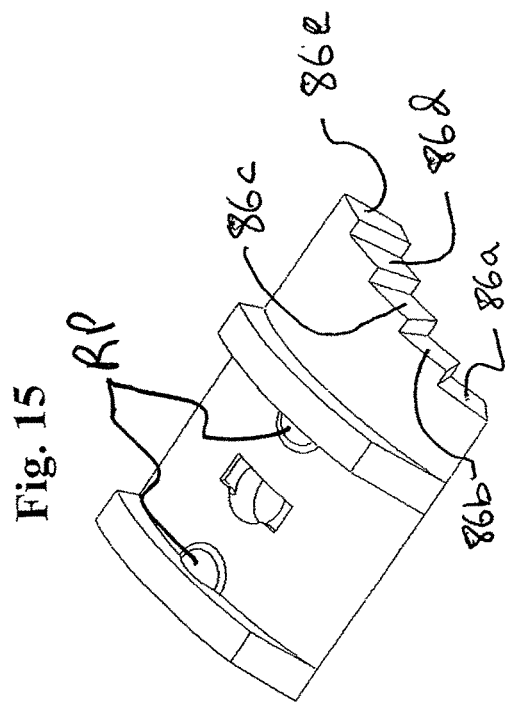

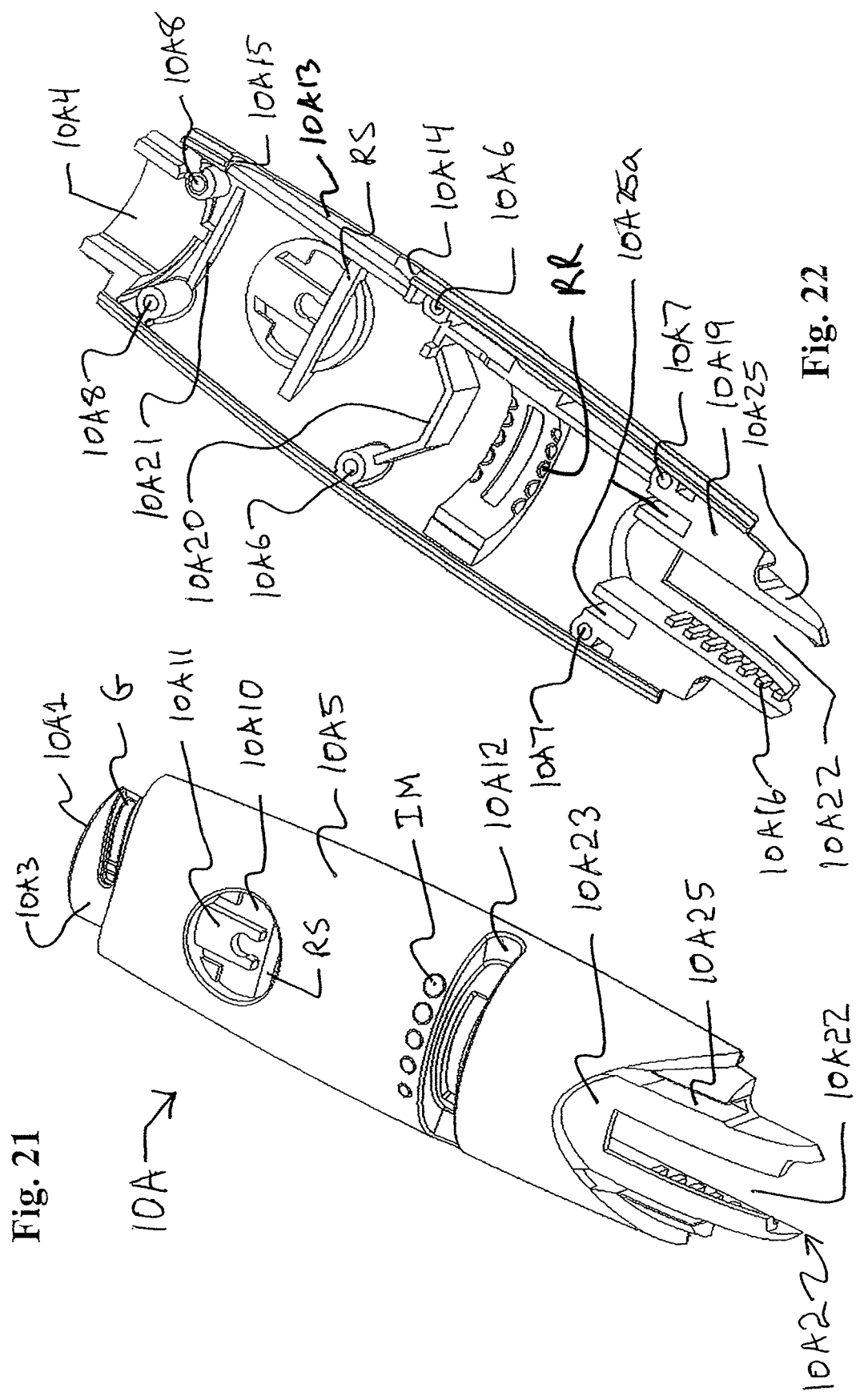

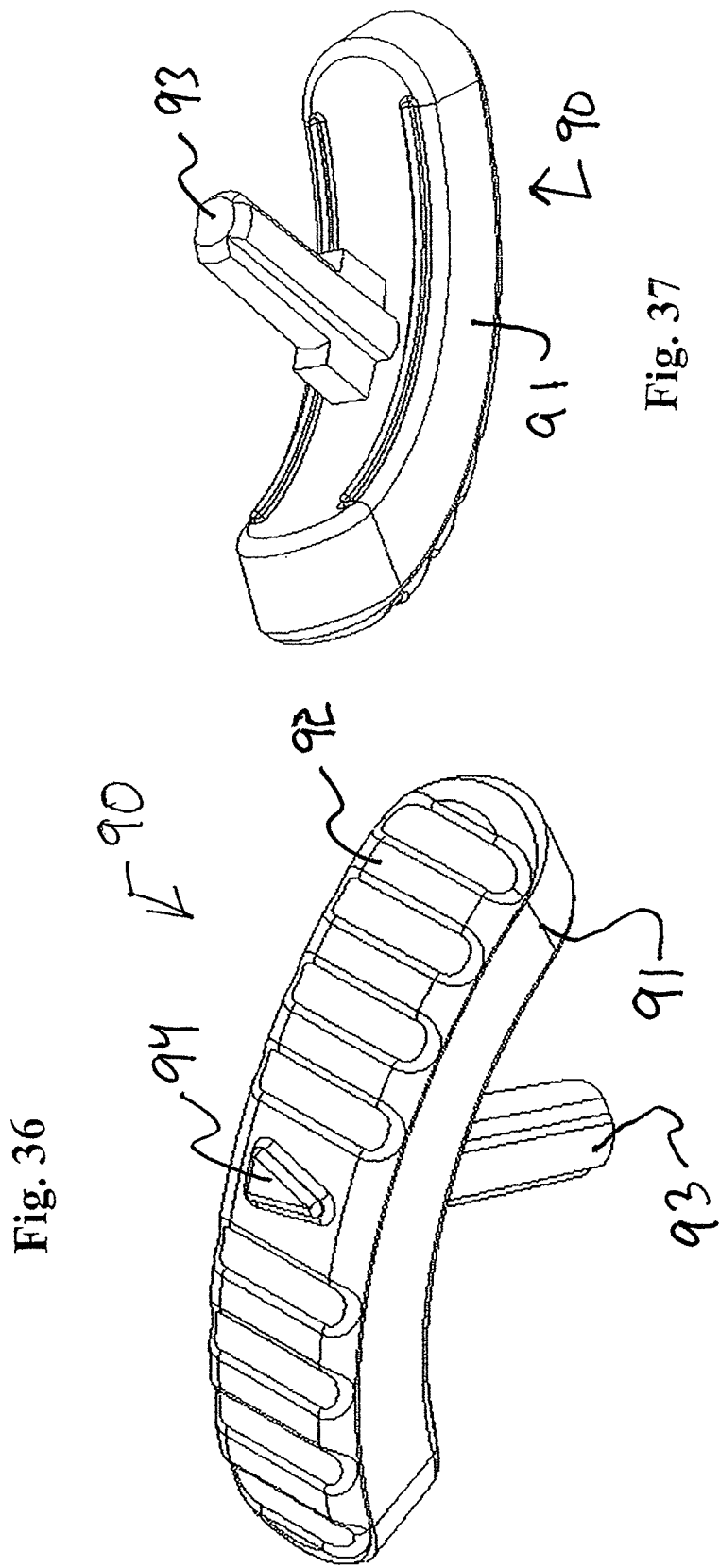

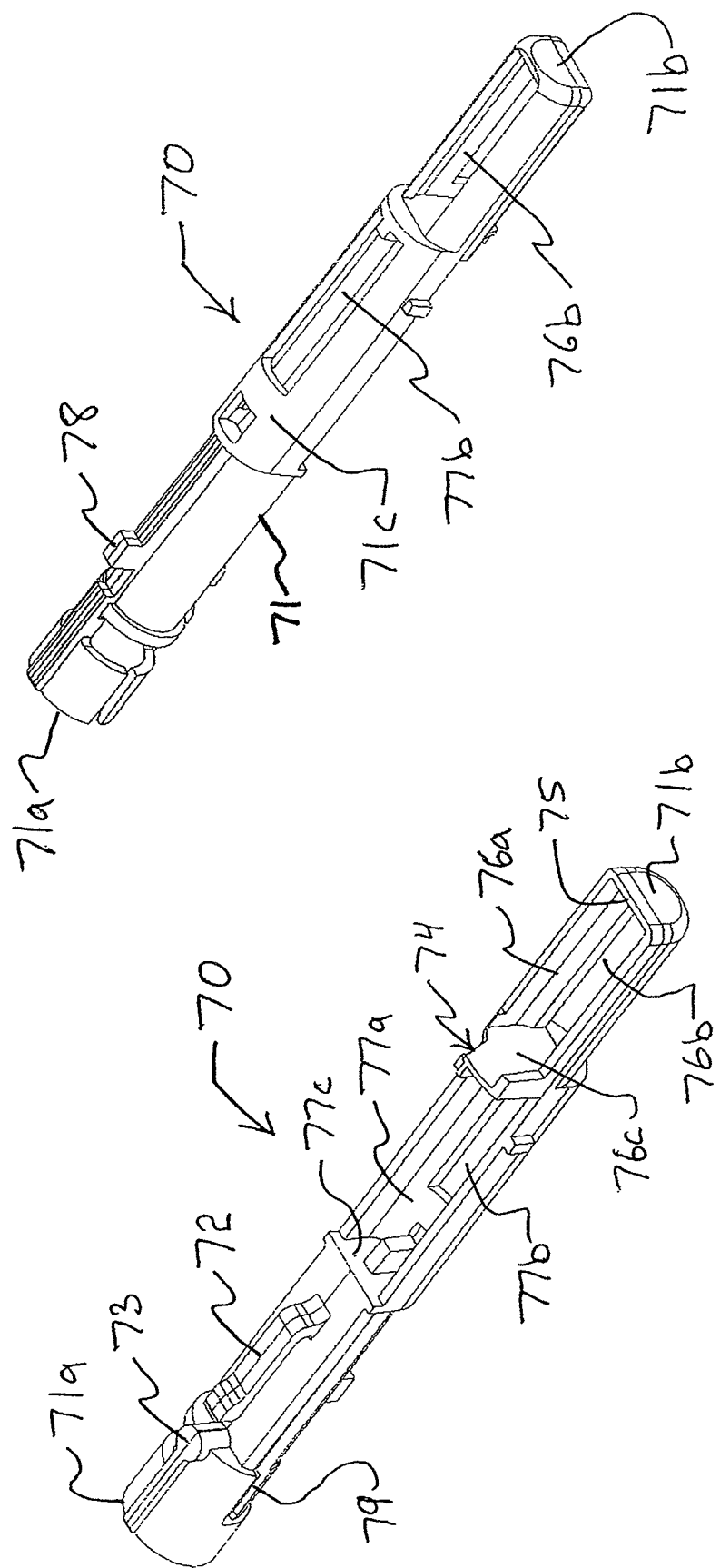

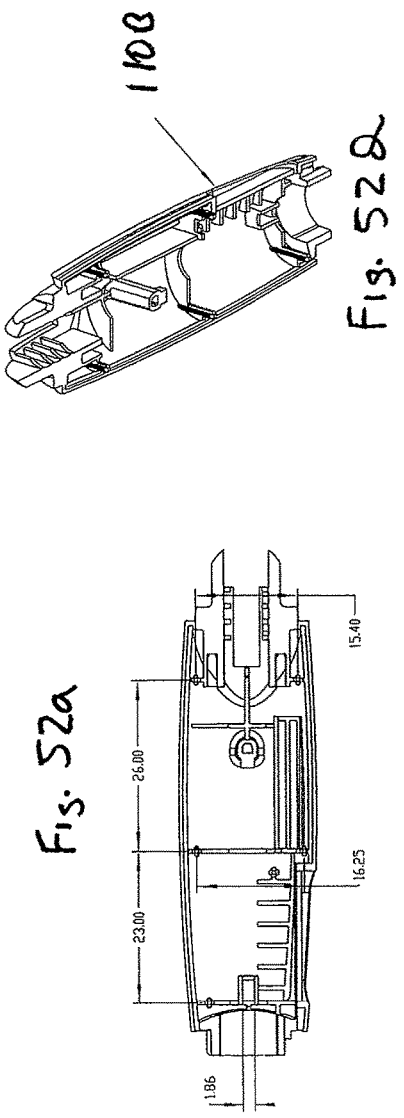
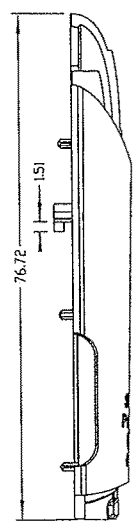
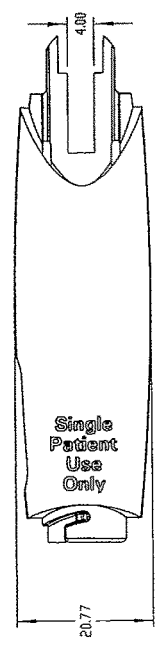
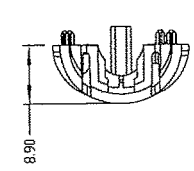
Fig. 52

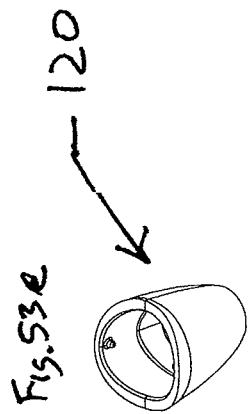
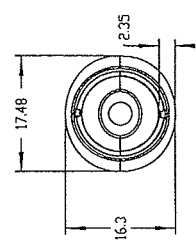
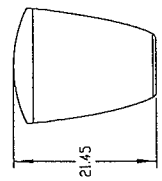
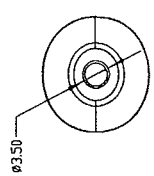
Fig. 53

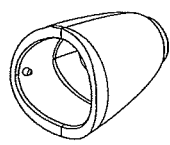
Fig. 54e
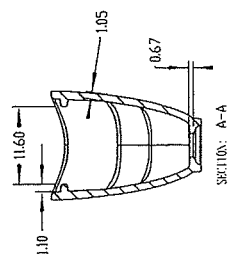
Fig. 54d
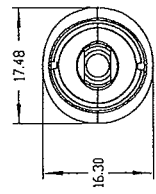
Fig. 54a
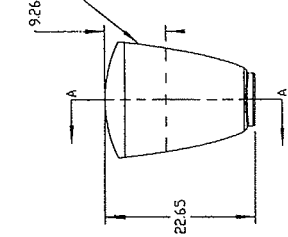
Fig. 54b
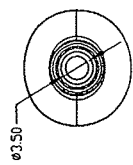
Fig. 54c
Fig. 54

Fig. 55
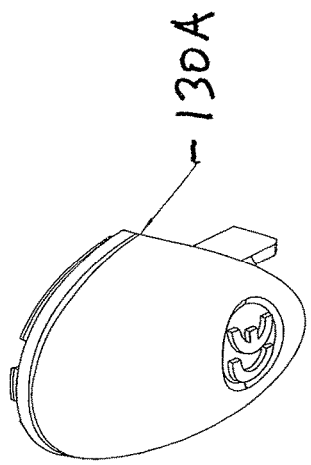
Fig. 55e
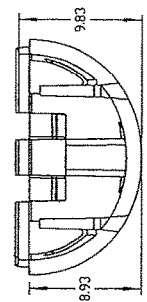
Fig. 55d
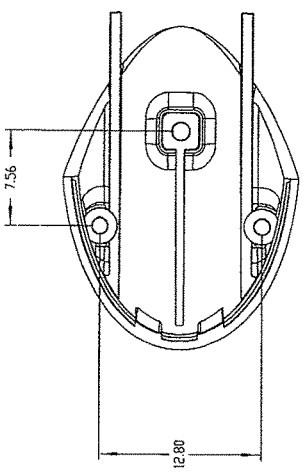
Fig. 55a
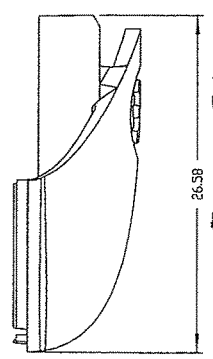
Fig. 55b
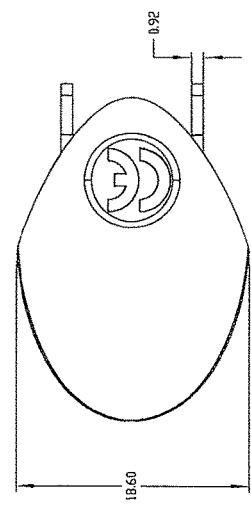
Fig. 55c

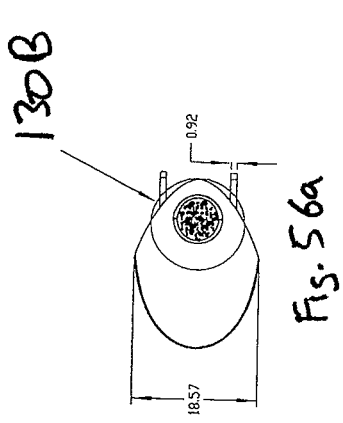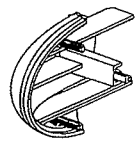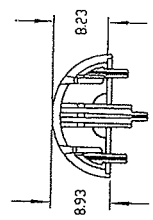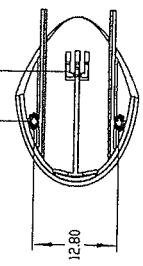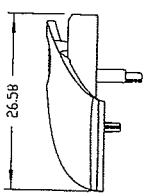
Fig. 56

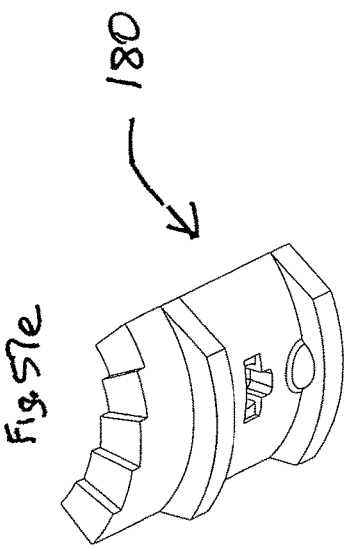
Fig. 57e
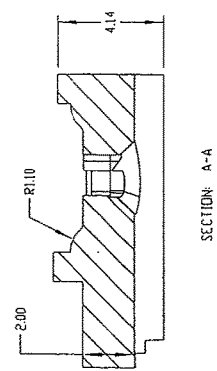
Fig. 57d
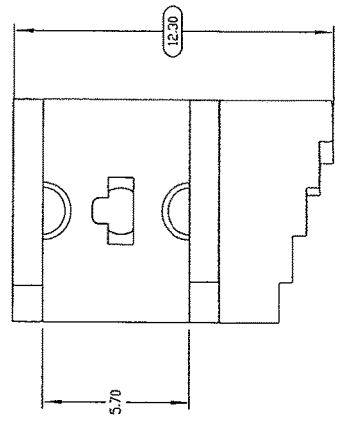
Fig. 57a
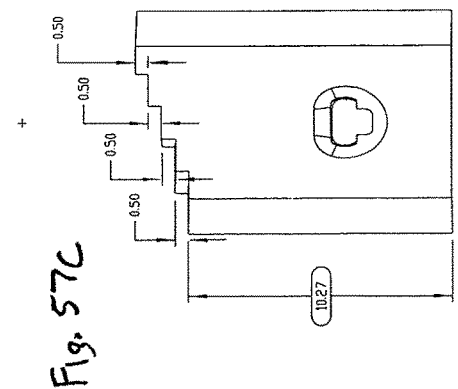
Fig. 57b   Fig. 57c
Fig. 57

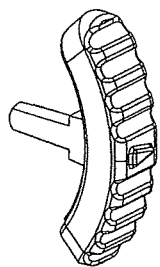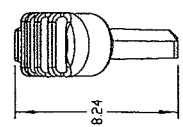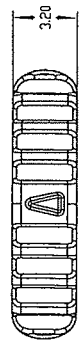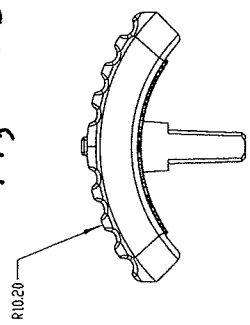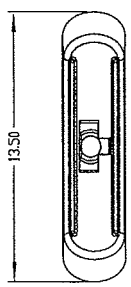
Fig. 58

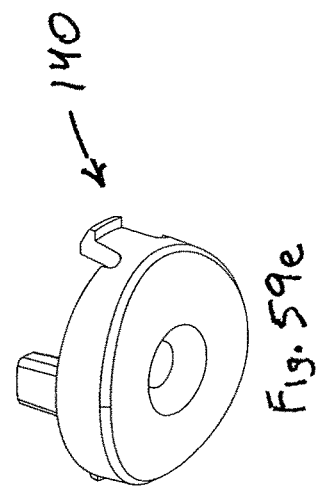
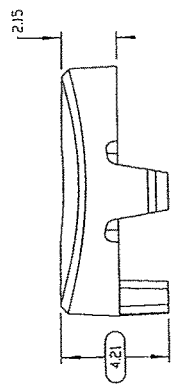
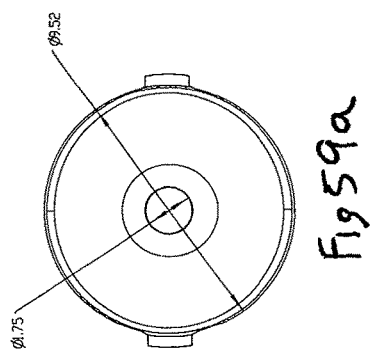
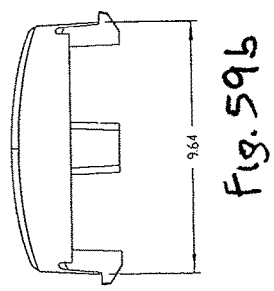
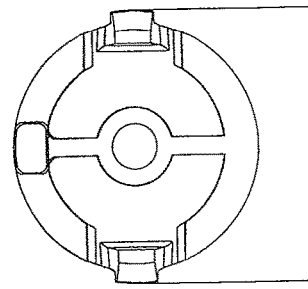
Fig. 59

Fig. 61
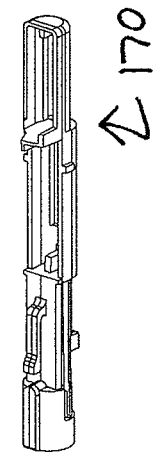
Fig. 61f
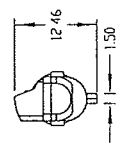
Fig. 61e
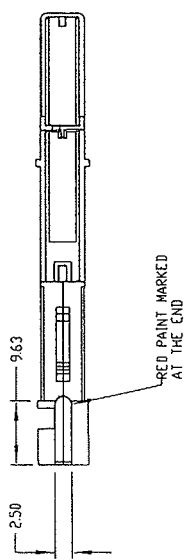
Fig. 61a
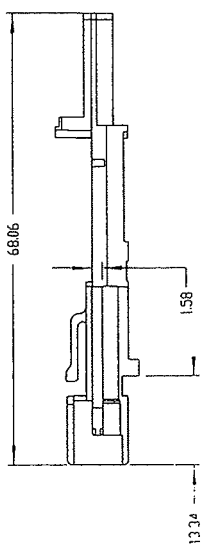
Fig. 61b
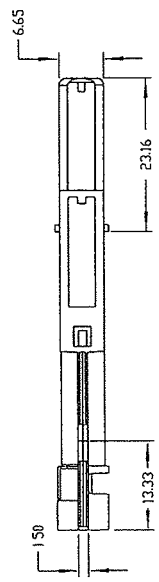
Fig. 61c
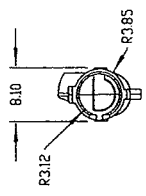
Fig. 61d Fig. 62
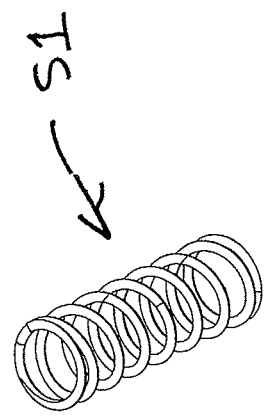
Fig. 62a
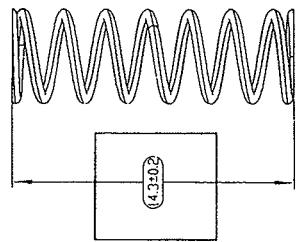
Fig. 62b
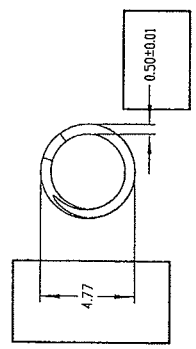
Fig. 62c Fig. 63
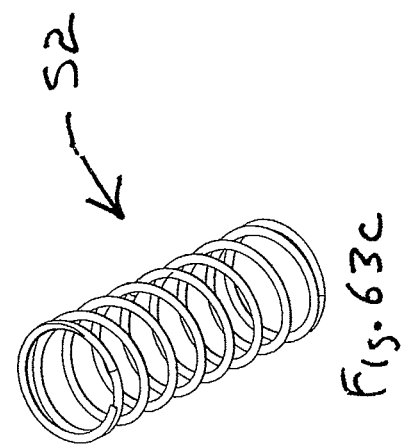
Fig. 63c
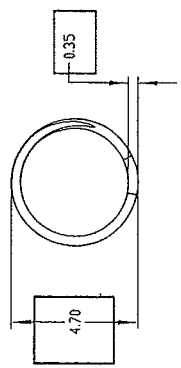
Fig. 63a
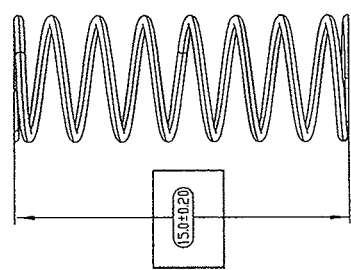
Fig. 63b

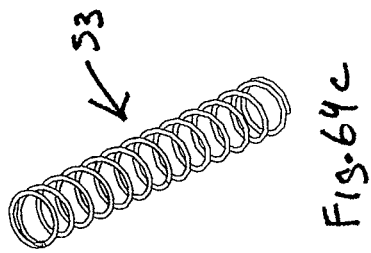
Fig. 64c
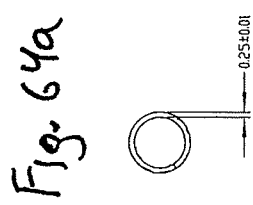
Fig. 64a
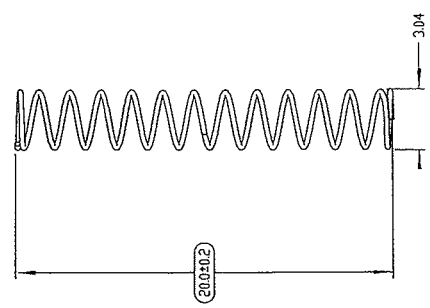
Fig. 64b
Fig. 64

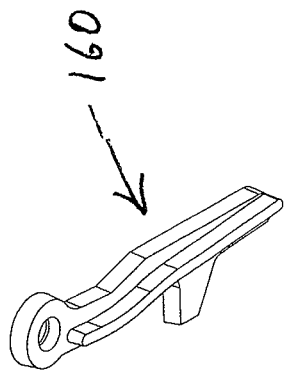
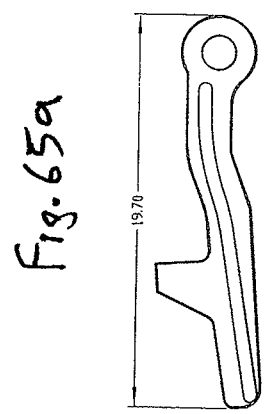
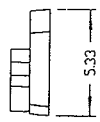
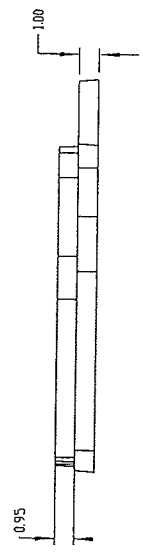
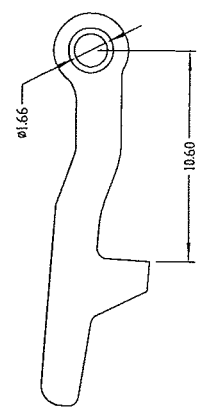
Fig. 65

LANCET DEVICE WITH DEPTH ADJUSTMENT AND LANCET REMOVAL SYSTEM AND METHOD

CROSS-REFERENCE TO RELATED APPLICATIONS

The instant application is a divisional of U.S. non-provisional application Ser. No. 14/748,768, filed Jun. 24, 2015, which claims priority to and the benefit of U.S. provisional application No. 62/017,433, filed Jun. 26, 2014, the disclosures of both of these are hereby expressly incorporated by reference in their entireties.

BACKGROUND OF THE INVENTION

1. Field of the Invention

The invention relates to a lancet device which utilizes depth adjustment and a lancet removal system. Lancet devices are used to penetrate and puncture the skin in order to allow the taking of a blood sample for testing. The present device allows the user to more safely remove and replace a lancet after each use.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like. Typical lancet devices also require the user to handle the lancet during replacement and installation.

An improved device would allow the user to more easily adjust the depth of penetration and would overcome some of the disadvantages described above. Moreover, since the skin thickness can vary slightly from user to user and finger to finger, a need exists for efficiently adapting the depth of penetration. For example, an index finger may be more calloused than a middle finger, and the more calloused finger will typically have thicker skin. By adjusting the depth of puncture so that the depth is no greater than necessary for extracting a required amount of blood, any pain experienced by the user may be minimized. The present device allows the user to more safely remove and replace a lancet after each use.

What is needed is a lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices. What is also needed is a lancet device which does not require the user to handle the lancets so as to prevent inadvertent pricking of the user's skin.

SUMMARY OF THE INVENTION

The instant application aims to improve the device disclosed in U.S. Patent Application Publication No. 2010/0274273 (U.S. Ser. No. 12/665,600 filed Jun. 18, 2008) published on Oct. 28, 2010, the disclosure of which is hereby expressly incorporated by reference hereto in its entirety.

According to one illustrative aspect of the invention there is provided a lancet device comprising a depth adjustment system having at least one element as disclosed or shown herein.

According to one illustrative aspect of the invention, the depth adjustment system includes at least element 80.

According to one illustrative aspect of the invention, the depth adjustment system includes at least element 90.

According to one illustrative aspect of the invention, the depth adjustment system includes at least elements 80 and 90.

According to one illustrative aspect of the invention there is provided a lancet device comprising a housing, a removable front cap mounted to the housing, a lancet holding member, a trigger and an arming system comprising a grippable cocking member structured and arranged to place the lancet device in a trigger-set or armed position. A depth adjustment system comprises a member that is at least slidable and partially rotatably mounted and that has an axis of rotation arranged substantially parallel to a center axis of the lancet holding member. An ejection system comprises an ejector having a portion extending outside a sidewall opening of the housing and being located closer to a front end of the housing than to a rear end of the housing. The sidewall opening of the housing is arranged on an area of the housing located between the trigger and a wall of the housing located opposite the trigger. The ejection system is structured and arranged to at least one of prevent axial movement of the lancet holding member or remove or eject a lancet from the lancet holding member.

According to one illustrative aspect of the invention, the portion extending outside a sidewall opening of the housing comprises a manually activated slide button.

According to one illustrative aspect of the invention, the ejection system each of prevents axial movement of the lancet holding member and removes or ejects the lancet from the lancet holding member.

According to one illustrative aspect of the invention, the member comprises plural cam or stop surfaces.

According to one illustrative aspect of the invention, the member comprises indicia.

According to one illustrative aspect of the invention, the member is arranged inside the housing and further comprising a selector button coupled to the member and being movable from outside the housing.

According to one illustrative aspect of the invention, the member is arranged inside the housing and further comprising a selector button coupled to the member and having a grip surface.

According to one illustrative aspect of the invention, the lancet device may further comprise a slide button or selector that is movable relative the hosing along a direction perpendicular to a longitudinal axis of the lancet device.

According to one illustrative aspect of the invention, the lancet device may further comprise a first spring configured to cause movement of the lancet holding member towards a puncturing position and a second spring configured to cause a back cap to move towards an initial position from a retracted position.

According to one illustrative aspect of the invention, the lancet device may further comprise a first spring configured to cause movement of the lancet holding member towards a puncturing position, a second spring configured to cause a back cap to move towards an initial position from a retracted position, and a third spring configured to cause a slide member of the ejection system to move towards an initial position from an extended position.

According to one illustrative aspect of the invention, there is provided a method of puncturing a surface of skin using the lancet device of anyone of types described above, wherein the method comprises arranging the lancet device adjacent against a user's skin and triggering the lancet device so that a lancet is caused to penetrate the user's skin.

According to one illustrative aspect of the invention there is provided a lancet device comprises a housing, a removable front cap mounted to the housing, a lancet holding member having a front end adapted to receive therein a removable lancet, a trigger and an arming system comprising a movable cocking member structured and arranged to place the lancet device in a trigger-set or armed position. A depth adjustment system comprises an arcuate-shaped member having plural cam surfaces. A lancet ejection system is located closer to a front end of the housing than to a rear end of the housing and comprises at least one of: a movement preventer configured to prevent axial movement of the lancet holding member; a lancet remover portion configured to remove or eject a lancet from the lancet holding member; or a front cap remover portion configured to remove or eject the front cap.

According to one illustrative aspect of the invention, the ejection system comprises a manually activated slide button.

According to one illustrative aspect of the invention, the ejection system each of prevents axial movement of the lancet holding member, removes or ejects the lancet from the lancet holding member, and removes or ejects the front cap.

According to one illustrative aspect of the invention, the lancet device may further comprise indicia arranged on the housing.

According to one illustrative aspect of the invention, the lancet device may further comprise a first spring configured to cause movement of the lancet holding member towards a puncturing position and a second spring configured to cause a back cap to move towards an initial position from a retracted position.

According to one illustrative aspect of the invention, the lancet device may further comprise a first spring configured to cause movement of the lancet holding member towards a puncturing position, a second spring configured to cause a back cap to move towards an initial position from a retracted position, and a third spring configured to cause a slide member of the ejection system to move towards an initial position from an extended position.

According to one illustrative aspect of the invention, there is provided a method of puncturing a surface of skin using the lancet device, wherein the method comprises arranging the lancet device adjacent against a user's skin and triggering the lancet device so that a lancet is caused to penetrate the user's skin.

According to one illustrative aspect of the invention there is provided a lancet device comprising a housing having an ergonomic shape, a removable front cap mounted to the housing, a movably mounted lancet holding member having a front end adapted to receive therein a removable lancet, a trigger arranged on a side wall of the housing, and an arming system comprising a movable cocking member configured to place the lancet device in a trigger-set or armed position. A depth adjustment system comprises a slidable member having plural cam surfaces and being movable along a direction that is not parallel to a longitudinal axis of the lancet device. A locking member is configured to prevent axial movement of the lancet holding member. A lancet ejector is arranged closer to a front end of the housing than to a rear end of the housing and being configured to remove or eject a lancet from the lancet holding member. The cocking member is located behind the member with plural cam surfaces and the lancet ejector is located in front of the member with plural cam surfaces.

According to one illustrative aspect of the invention there is provided a lancet device comprising a housing, a removable front cap, a movably mounted lancet holding member having a front end adapted to receive therein a removable lancet, a trigger arranged on at least one of a lateral side of the lancet device or a side wall of the housing. An arming system is configured to place the lancet device in a trigger-set or armed position. The arming system comprises a cocking member arranged at a rear end of the housing that can move away from the housing when the lancet device is placed in the trigger-set or armed position. A first spring is configured to move the lancet holding member to a puncturing position. A second spring that is compressed when the member is moved away from the housing. An ejection system is configured to remove or eject a lancet from the lancet holding member. The ejection system comprises a slidable ejector including each of a first portion that extends outside the housing and that can be moved by a user, a second portion adapted to extend into a portion of the lancet holding member and to contact the removable lancet when installed therein, and a third portion that can slide over a front cap mounting portion of the lancet device when the front cap is removed from the front cap mounting portion and when the slidable ejector is slid to an ejection position. A curved depth adjustment member is arranged within the housing and being movable along a curved path between plural depth of penetration setting positions.

According to one illustrative aspect of the invention, the lancet device may further comprising a locking member configured to prevent axial movement of the lancet holding member.

According to one illustrative aspect of the invention, the front cap is removable when rotated relative to the housing and the lancet holding member comprises a deflecting portion that can be contacted by a portion of the trigger.

According to one illustrative aspect of the invention, the slidable ejector and the trigger are each arranged at least one of closer to the front end than to the rear end of the housing or closer to a front end than to a rear end of the lancet device.

The invention also provides for a lancet device of the type disclosed herein whose parts utilize the same materials as the materials of corresponding parts of U.S. Ser. No. 10/441,065 to SCHRAGA filed May 20, 2003, the disclosure of this document is hereby expressly incorporated by reference in its entirety.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 7 shows a partial view of a front portion of the device of FIG. 1 with the front cap removed and after the lancet ejection system has been moved to a lancet ejection position;

FIG. 8 shows a cross-section view of the front portion shown in FIG. 7 after the lancet ejection system has been allowed to move to an initial position;

FIG. 9 shows a cross-section view of the front portion shown in FIG. 7;

FIG. 13 shows an enlarged side cross-section view of a middle portion of the lancet device of FIG. 2 and illustrates the depth adjustment system—prior to triggering;

FIG. 14 shows an enlarged side cross-section view of a middle portion of the lancet device of FIG. 4 and illustrates the depth adjustment system—post triggering;

FIG. 15 shows a bottom side perspective view of the depth adjustment member shown in FIGS. 13 and 14;

FIG. 21 shows a perspective outside view of the upper housing part shown in FIG. 20;

FIG. 22 shows a perspective inside view of the upper housing part shown in FIG. 21;

FIGS. 36 and 37 show perspective front and back side views of the slider or push-button portion of the depth adjustment system used in the embodiment of FIG. 1;

FIG. 43 shows a top left-side perspective view of FIG. 42;

FIG. 44 shows a bottom right-side perspective rear side view of FIG. 43;

FIGS. 52 and/or 52a-52e show various view of a non-limiting commercial embodiment of a lower body portion having certain identified dimensions in millimeters and used on the lancet device of FIG. 50;

FIGS. 53 and/or 53a-53e show various view of a non-limiting commercial embodiment of a front cap having certain identified dimensions in millimeters and used on the lancet device of FIG. 50;

FIGS. 54 and/or 54a-54e show various view of a non-limiting commercial embodiment of an alternate site testing (AST) type alternative front cap having certain identified dimensions in millimeters and used on the lancet device of FIG. 50;

FIGS. 55 and/or 55a-55e show various view of a non-limiting commercial embodiment of an upper back cap portion having certain identified dimensions in millimeters and used on the lancet device of FIG. 50;

FIGS. 56 and/or 56a-56e show various view of a non-limiting commercial embodiment of a lower back cap portion having certain identified dimensions in millimeters and used on the lancet device of FIG. 50;

FIGS. 57 and/or 57a-57e show various view of a non-limiting commercial embodiment of a depth adjustment member having certain identified dimensions in millimeters and used on the lancet device of FIG. 50;

FIGS. 58 and/or 58a-58e show various view of a non-limiting commercial embodiment of a slider depth adjuster having certain identified dimensions in millimeters and used on the lancet device of FIG. 50;

FIGS. 59 and/or 59a-59e show various view of a non-limiting commercial embodiment of a trigger button having certain identified dimensions in millimeters and used on the lancet device of FIG. 50;

FIGS. 61 and/or 61a-61f show various view of a non-limiting commercial embodiment of a lancet holder having certain identified dimensions in millimeters and used on the lancet device of FIG. 50;

FIGS. 62 and/or 62a-62c show various view of a non-limiting commercial embodiment of a first or drive spring having certain identified dimensions in millimeters and used on the lancet device of FIG. 50;

FIGS. 63 and/or 63a-63c show various view of a non-limiting commercial embodiment of a second or return spring having certain identified dimensions in millimeters and used on the lancet device of FIG. 50;

FIGS. 64 and/or 64a-64c show various view of a non-limiting commercial embodiment of a third or ejector spring having certain identified dimensions in millimeters and used on the lancet device of FIG. 50; and FIGS. 65 and/or 65a-65e show various view of a non-limiting commercial embodiment of a lock member having certain identified dimensions in millimeters and used on the lancet device of FIG. 50.

DETAILED DESCRIPTION OF THE PRESENT INVENTION

Figure 1:
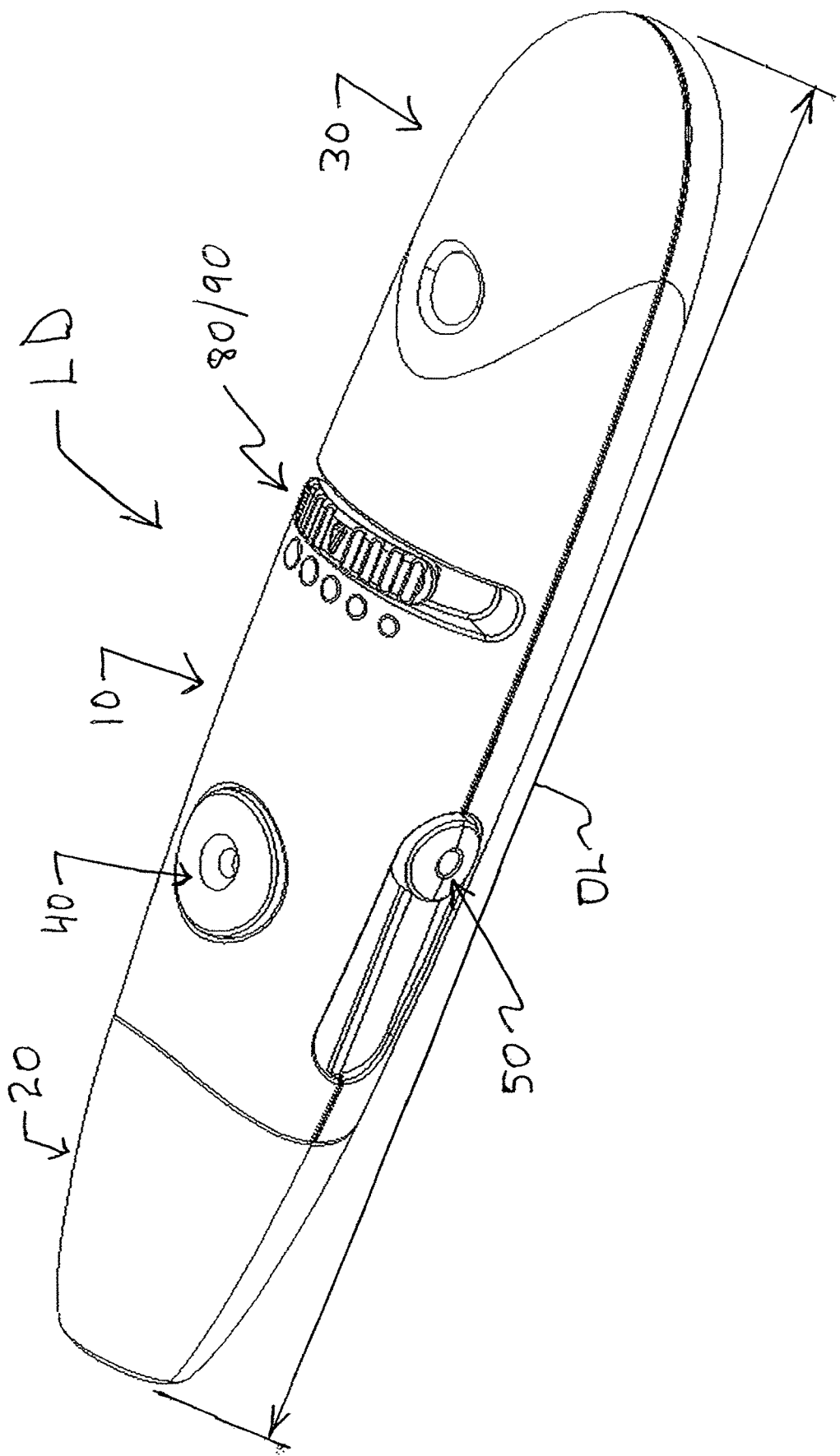
FIG. 1 shows a left front side perspective view of a non-limiting embodiment of the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-49 show one non-limiting embodiment of a lancet device LD. The lancet device LD includes the following main components: a housing or body 10 which preferably comprises housing parts 10A and 10B, a front cap 20, a back cap 30 which preferably comprises parts 30A and 30B, a trigger 40, a lancet advance ejection button or member 50, a locking member 60, a lancet holding member 70, a depth adjustment system utilizing members 80 and 90, and three springs $S_i$, $S_2$ and $S_3$.

As can be seen in FIG. 1, the lancet device LD can preferably have, by way of non-limiting example, an overall length OL which is approximately 5 inches and an overall width or diameter (measured over the device's largest portion) of approximately 1.25 inches. The lancet device LD also preferably has an ergonomic shape such that it can be held comfortably in a user's hand such that the user can move the depth adjustment member 80 by engaging member 90 with the user's thumb or index finger, as will be described in detail later on, to set the depth of penetration prior to use. The user can also depress and slide forward the advance button 50 in order cause a forward advance of a lancet and optionally simultaneously cause removal of the front cap 20, as will be described in detail later on. The user can also depress the trigger 40 with either the user's thumb of index finger. The only step which likely requires the user to use two hands, is the step of placing the lancet device LD is an armed or trigger-set position—which will be described in detail later on.

Figure 2:
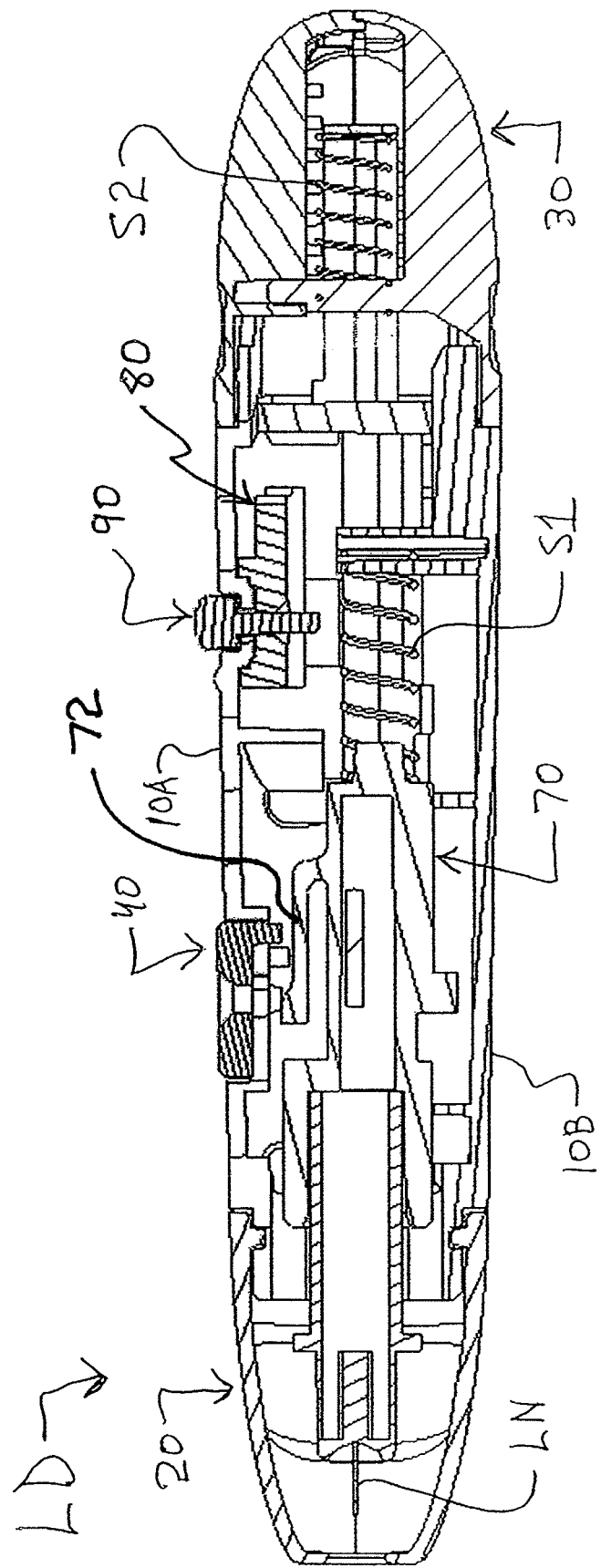
FIG. 2 shows a side cross-section view of FIG. 1. The device is shown in an initial or intermediate state.

As can be seen in FIG. 2, the lancet device LD locates a removable front cap 20 at a front or proximal end of the body 10 (10A/10B). When the lancet holding member 70 is in the intermediate position or static state shown in FIG. 2, the installed lancet extends more forward that front end of the body 10. The needle LN of the installed lancet, however, remains safely behind the skin engaging surface of the front cap 20. In this position, the trigger 40 cannot cause (even if depressed) skin puncturing because the delectable projecting portion 72 of the lancet holding member 70 is not yet in retaining engagement with the retaining shoulder RS (see FIG. 3) of the body 10. Moreover, in this position, the second spring $S2$ is slightly compressed while the first spring $S_i$ is essentially in a relaxed state. As the energy used for skin puncturing results from rapid axial expansion of the first spring $S_i$ from a compressed state and as the first spring $S_i$ is not in this compressed state, skin puncturing cannot yet occur. In this position, a user can also freely adjust a depth of penetration adjustment by moving the slide button 90 to a desired depth of penetrating setting position. The slightly compressed state of the second spring $S2$ results from the first spring $S_i$ being in the largely relaxed state and the second spring $S2$ also functions to bias the back cap 30 toward its original, non-extended or un-cocked position shown in FIG. 2.

Figure 3:
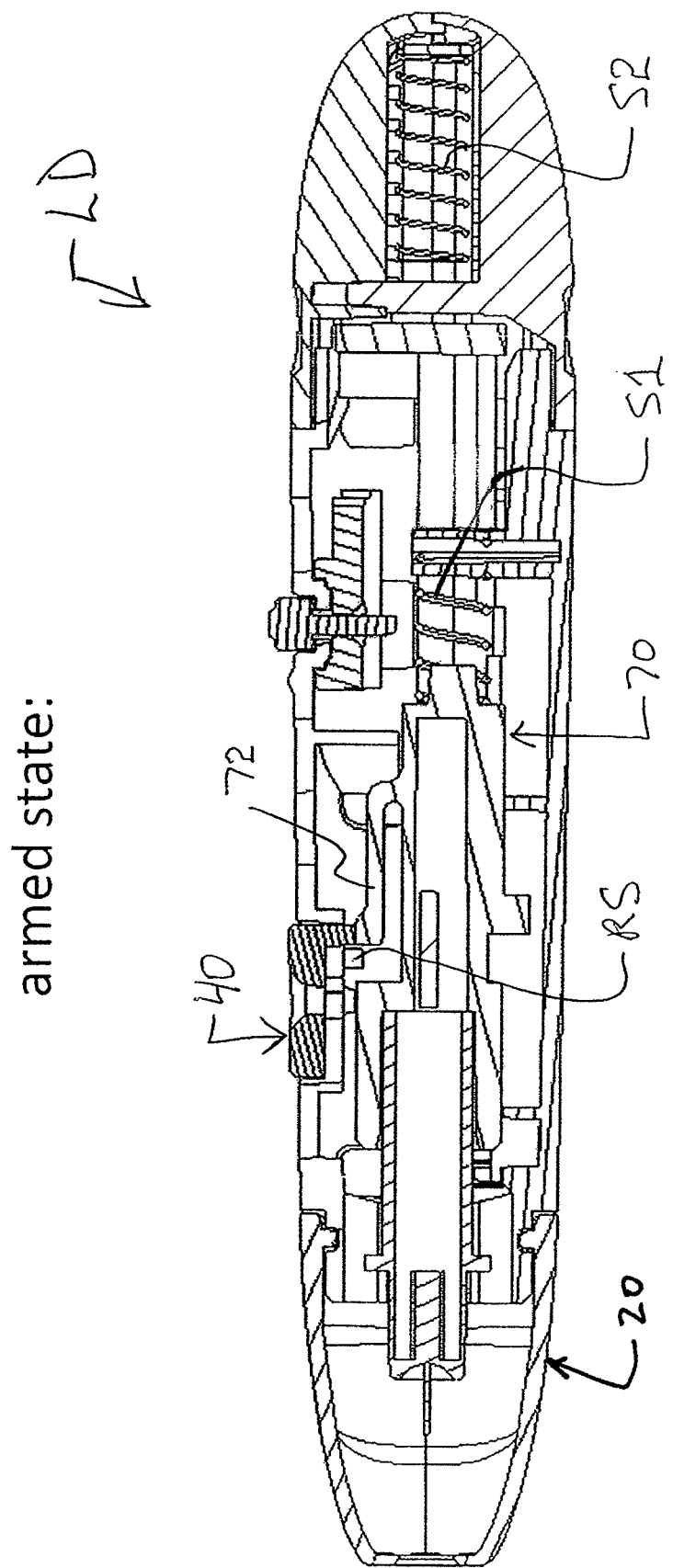
FIG. 3 shows a side cross-section view of FIG. 2 after the device is placed in an arming or trigger-set position.

As can be seen in FIG. 3, when the lancet holding member 70 is in the trigger-set position or armed state shown in FIG. 3, the installed lancet still extends more forward that front end of the body 10, but by a lesser amount than in FIG. 2. The needle LN of the installed lancet, however, remains well safely behind the skin engaging surface of the front cap 20. In this position, the trigger 40 can cause (if depressed) skin puncturing because the delectable projecting portion 72 of the lancet holding member 70 is in retaining engagement with the retaining shoulder RS of the body 10. Moreover, in this position, the second spring $S2$ is very slightly compressed or largely in a relaxed state while the first spring $S_i$ is essentially in a maximum compressed state. As the energy used for skin puncturing results from rapid axial expansion of the first spring $S_i$ from the compressed state and as the first spring $S_i$ is in this compressed state, skin puncturing can occur as soon as the trigger 40 is depressed and the deflectable projection 72 is caused by the trigger 40 to disengage from the retaining shoulder RS. Although not recommended, in this position, a user may be able to freely adjust a depth of penetration adjustment by moving the slide button 90 to a desired depth of penetrating setting position. The largely relaxed state of the second spring S2 results from the holding member 70 being located or retained in a maximum rearward position. However, even in this position, the second spring S2 functions to bias the back cap 30 toward its original, non-extended or un-cocked position shown in each of FIGS. 2 and 3. In order to place the lancet device LD in the armed position shown in FIG. 3, the user will typically grip the body 10 with one hand while in the position shown in FIG. 2, and using the other hand, will pull back on the back cap 30 to move it back and away from the body 10 until the deflectable projection 72 is caused to engage with the retaining shoulder RS. When this engagement occurs, the user can release the back cap 30—which will be caused to move forward or toward the body 10 until it reaches the position shown in FIGS. 2 and 3.

Figure 4:
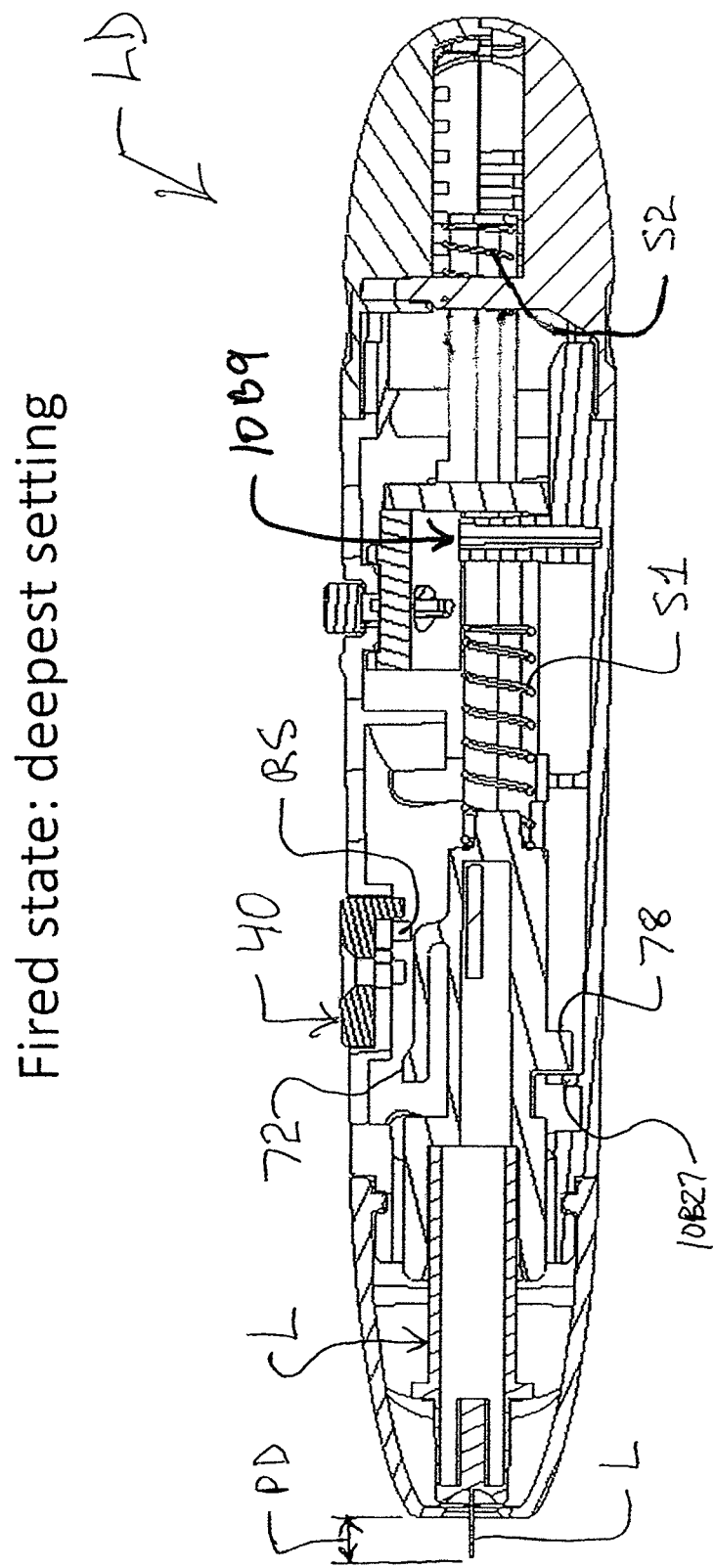
FIG. 4 shows a side cross-section view of FIG. 2. The device is shown in a triggered state and before the lancet holding member is automatically moved back to the position shown in FIG. 2.

As can be seen in FIG. 4, the lancet holding member 70 can be caused to move to the puncturing position shown in FIG. 3 upon triggering. In this position, the installed lancet still extends more forward that front end of the body 10 by essentially a maximum amount compared to FIG. 2. The needle LN of the installed lancet no longer remains well safely behind the skin engaging surface of the front cap 20, but instead projects out past the skin engaging surface by a puncturing depth PD. This, of course, is a very momentary position, i.e., occurring in a fraction of a second. If fact, it occurs so quickly that the trigger 40 will typically remain depressed (or in contact with a trigger finger) after causing the delectable projecting portion 72 of the lancet holding member 70 to disengage from the retaining shoulder RS of the body 10. Moreover, in this position, the second spring S2 reaches a maximum compressed state while the first spring Si is essentially in a maximum expanded state. Indeed, as the energy used for skin puncturing results from rapid axial expansion of the first spring Si from the compressed state and as the first spring Si is now no longer in the compressed state, after skin puncturing, axial expansion of the second spring S2 will function to cause the holding member 70 to move back to the intermediate position shown in FIG. 2. Although not shown, immediately after reaching the puncturing position shown in FIG. 4 the lancet device will again assume the position shown in FIG. 2. Of course, the amount of the puncturing depth PD can vary depending in the set position of the button 90. If, for example, the button 90 is slid all the way over to one side, the depth PD can be a maximum puncturing depth amount. If, on the other hand, the button 90 is slid all the way over to the opposite side, the depth PD can be a minimum puncturing depth amount. Positions intermediate these extremes represent increasing/decreasing depths PD. When in depth PD is at its maximum, the projection 78 of the holding member 70 will be at its closest to the projection or shoulder 10827 of the body 10.

Figure 6:
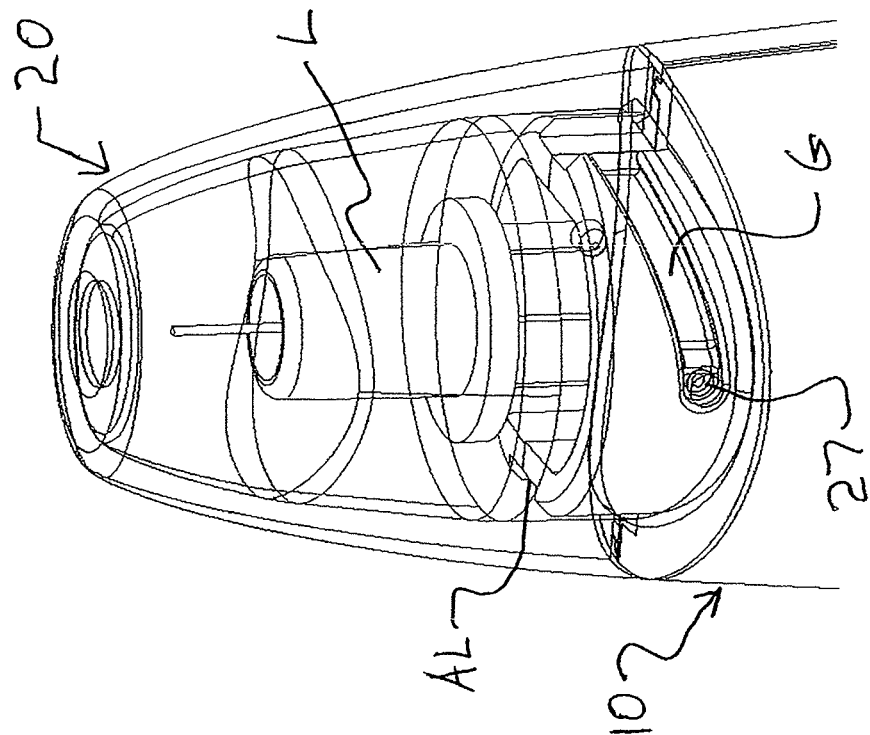
FIGS. 5 and 6 show an enlarged partial views of a front portion of the lancet device shown in FIG. 1 with the front cap being represented as transparent.
Figure 5:
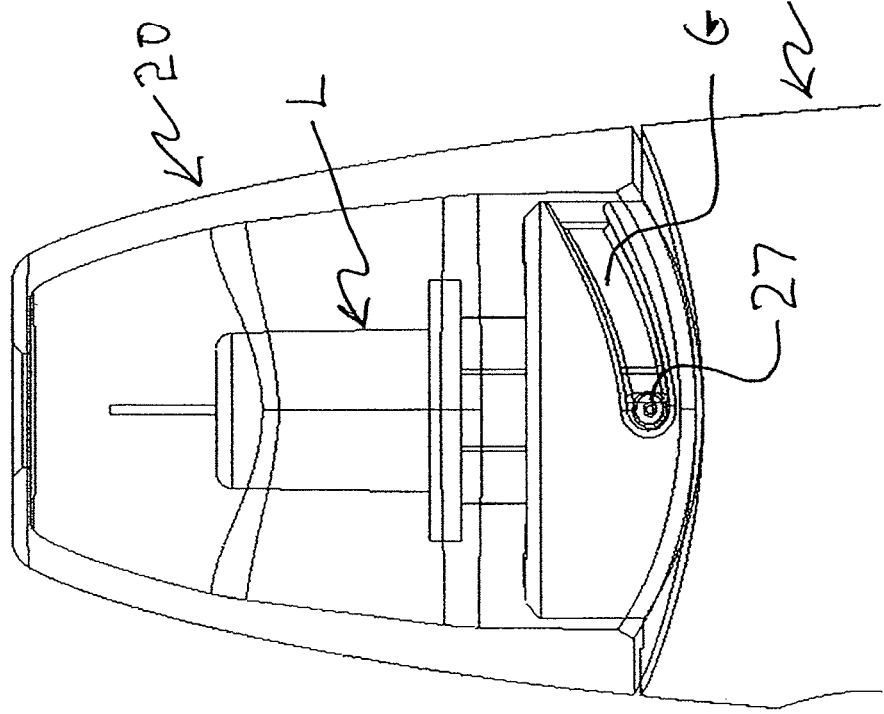
Figure 27:
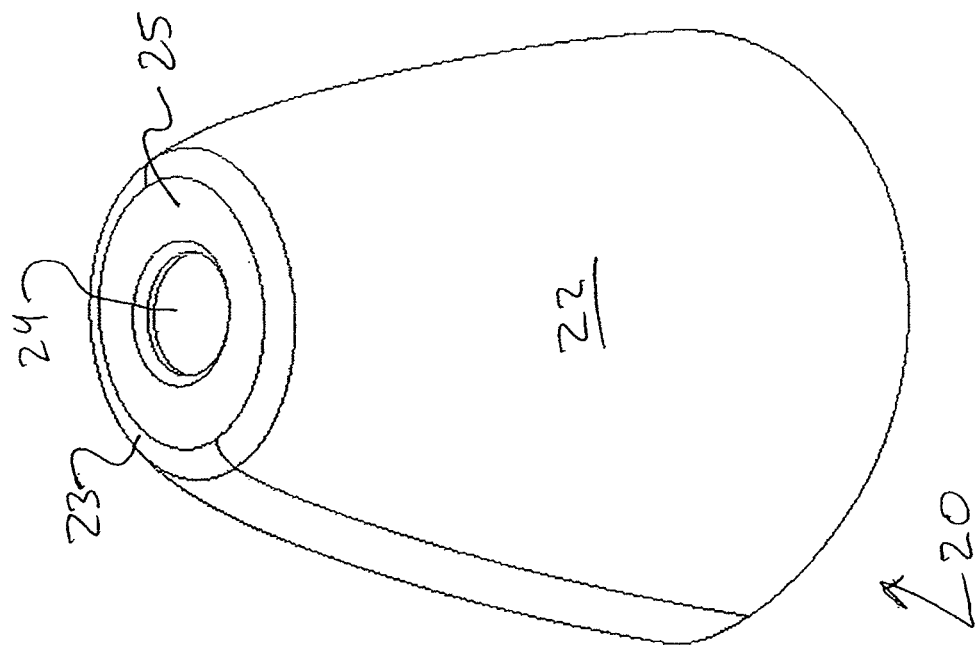
FIG. 27 shows a perspective outside view of the front cap shown in FIG. 26.
Figure 26:
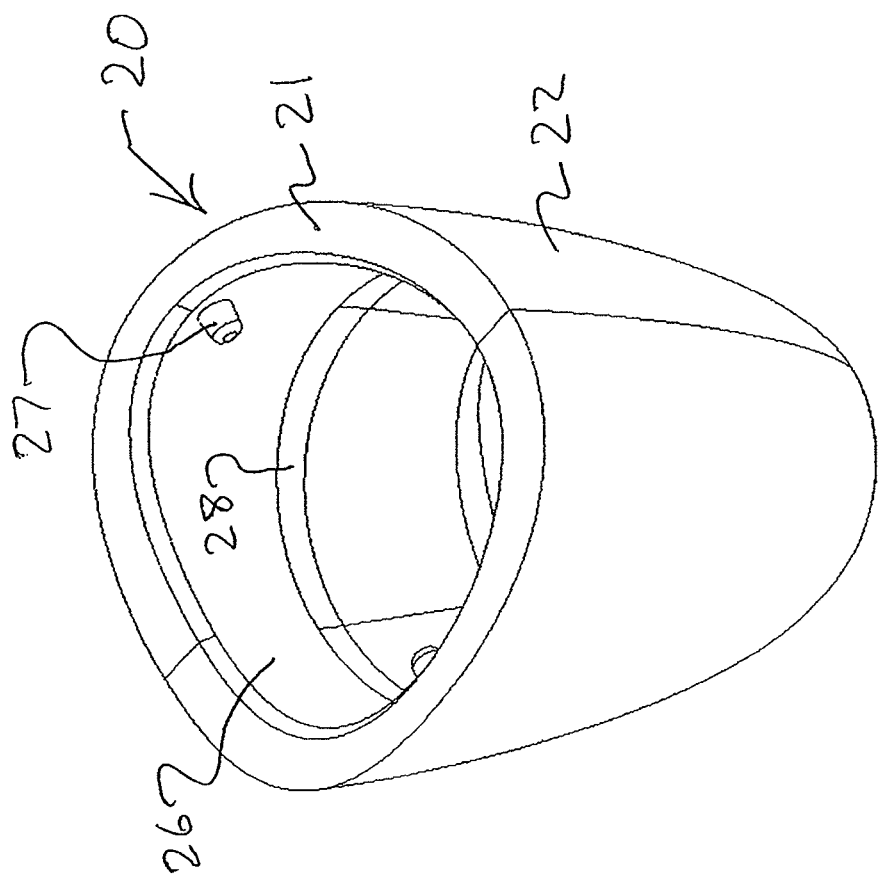
FIG. 26 shows a perspective inside view of the front cap used in the lancet device shown in FIG. 1.
Figure 41:
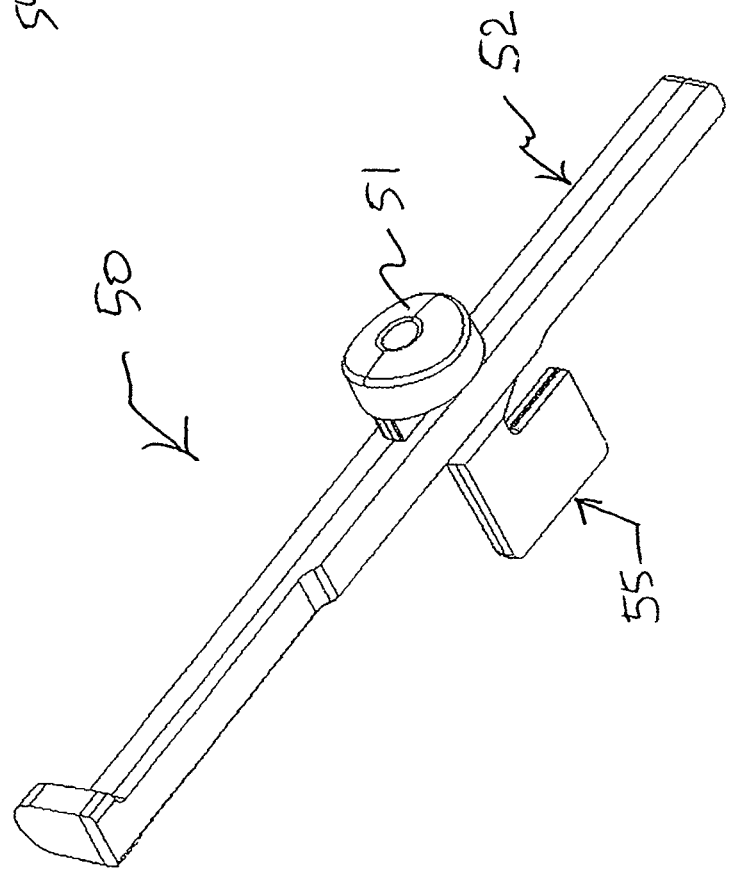
Figure 42:
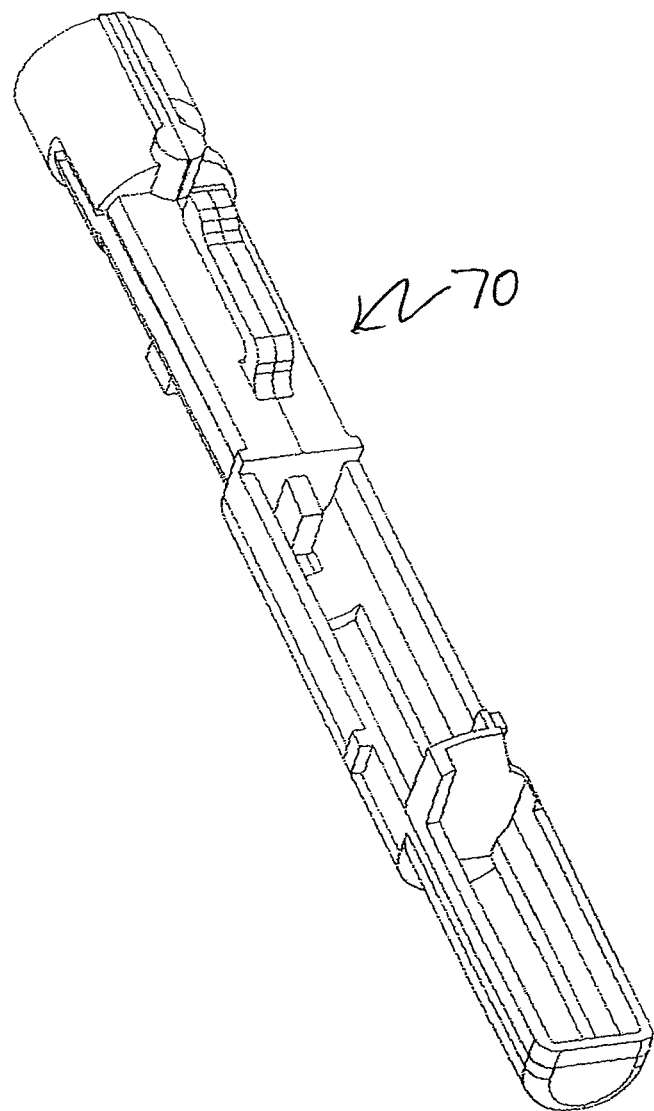
FIG. 42 shows a top perspective view of the lancet holding member used in the lancet device shown in FIG. 1.

As can be seen in FIGS. 5 and 6, the front cap 20 is removably installable on a front portion of the body 10. To secure the same, a user slides on the front cap 20, with the inward protruding oppositely arranged projections 27, aligned with receiving portions or alignment grooves AL of the respective grooves G of the body 10. Thereafter, the user then partially rotates the front cap 20 so that the projections 27 engage with the helical portions of the grooves G. The user will typically remove the front cap 20 before or after use to replace or install a lancet L. The front cap 20 also forms that part of the lancet device that is placed in contact with a skin that will be punctured. With reference to FIGS. 26 and 27, this occurs when the skin engaging surface 25 is placed in contact with skin or tissue. Triggering of the lancet device will then cause the needle of the lancet L to pass through the opening 24. The surface 25 transitions at a rounded edge 23 to a tapered main surface or portion 22. The internal shoulder 28 is configured to abut or closely approach a front end of the body 10 whereas the end 21 is configured to abut or closely approach the shoulder of the body 10 located behind the grooves G. The generally cylindrical inner surface 26 is sized to rotatably slide over the generally cylindrical surface of the body 10 which includes therein or thereon the grooves G. Additional details of the ejector 50 are shown in FIGS. 41 and 42 which show the slide button portion 51, a forward projecting portion 52 having forward end 53, an opposite or rear projection 54 that engages with the spring S3, the pushing portion 55 having lancet engaging end or edge 58, the lock engaging portion 56 having a camming groove 57.

Figure 10:
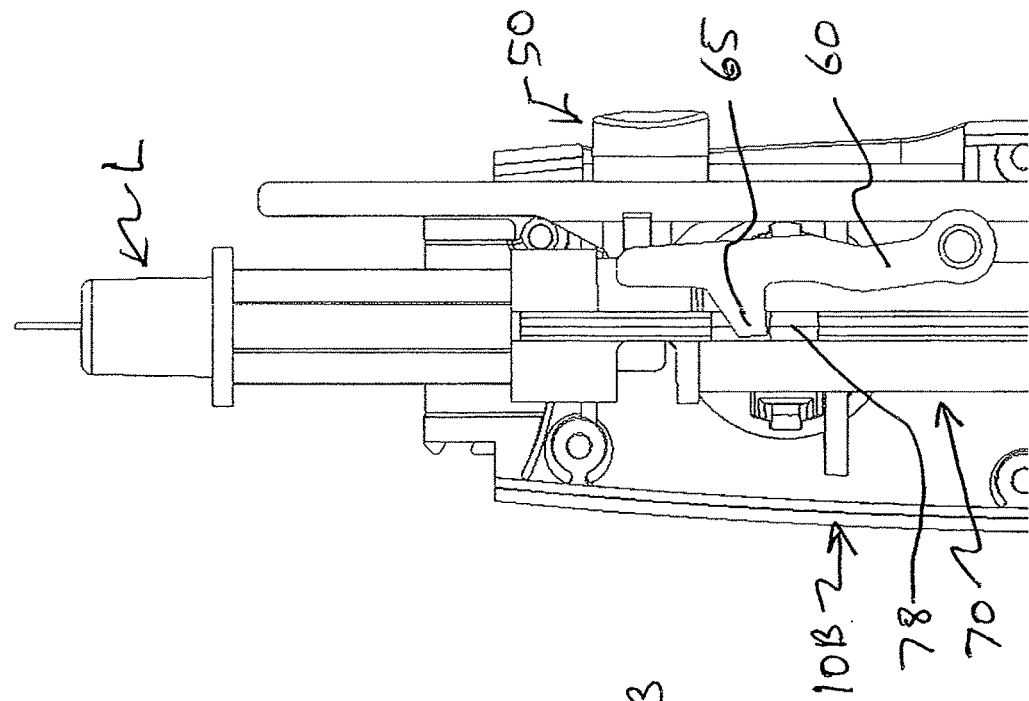
FIG. 10 shows a bottom partial view of a front portion (bottom housing part removed) of the device of FIG. 1 with the front cap removed and after the lancet ejection system has been moved to a lancet ejection position.
Figure 11:
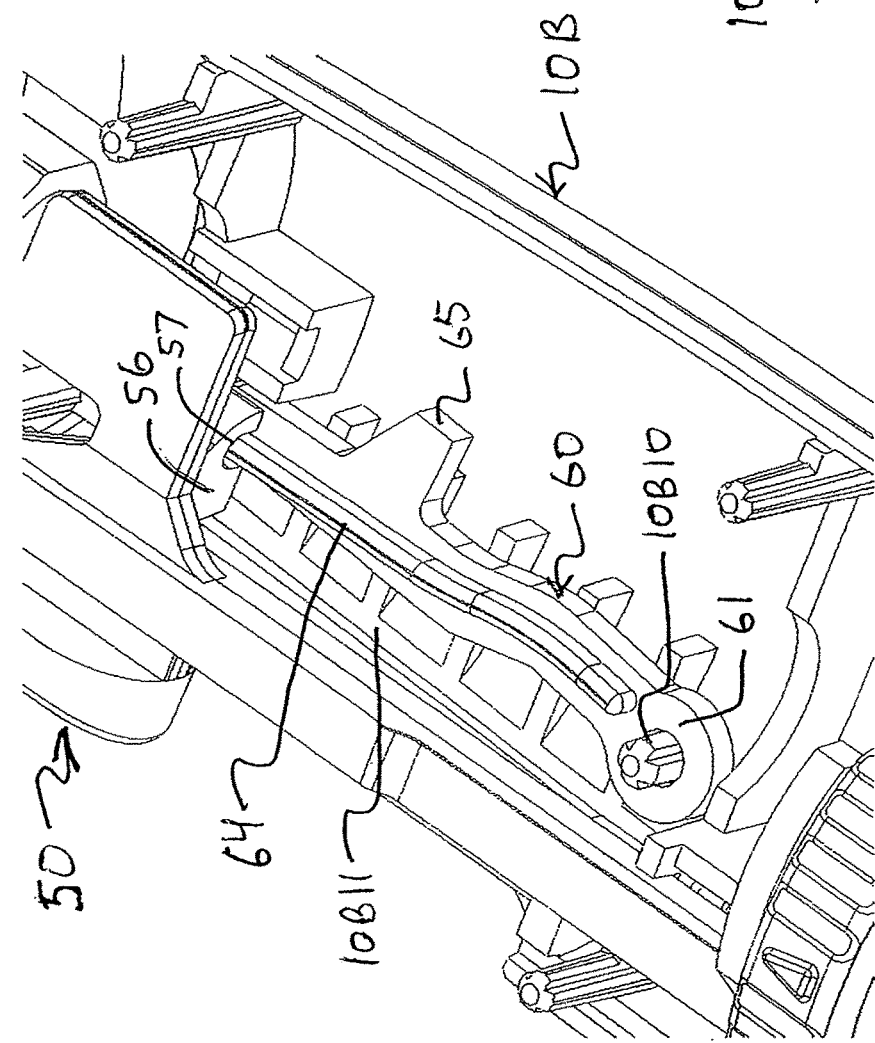
FIG. 11 shows a top partial view of a front portion (top housing part and lancet holding member removed) of the device of FIG. 1 with the front cap removed and after the lancet ejection system has been moved to a lancet ejection position.
Figure 12:
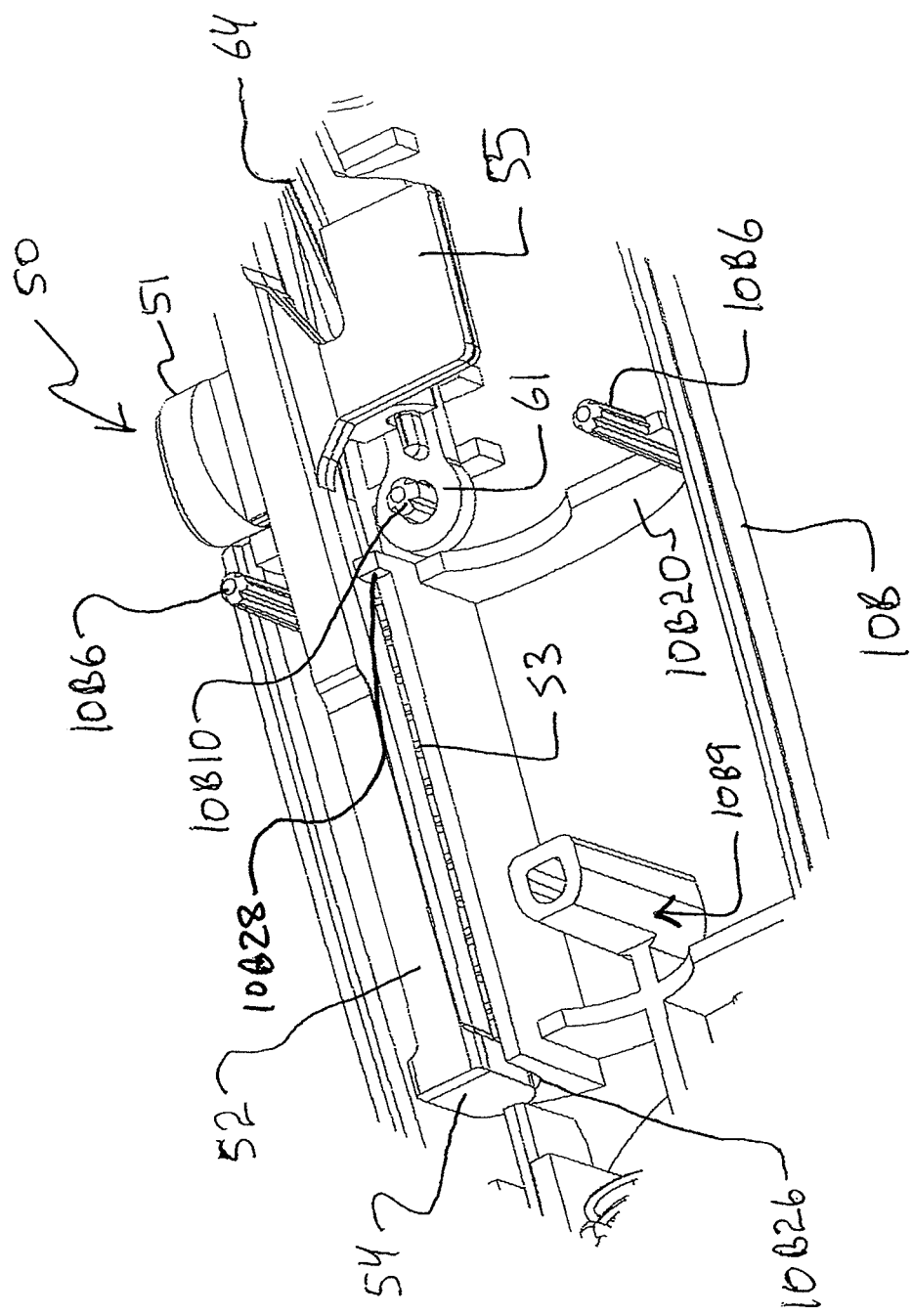
FIG. 12 shows a top partial view of a middle portion (top housing part and lancet holding member removed) of the device of FIG. 1 with the lancet ejection system in an initial position.
Figure 49:
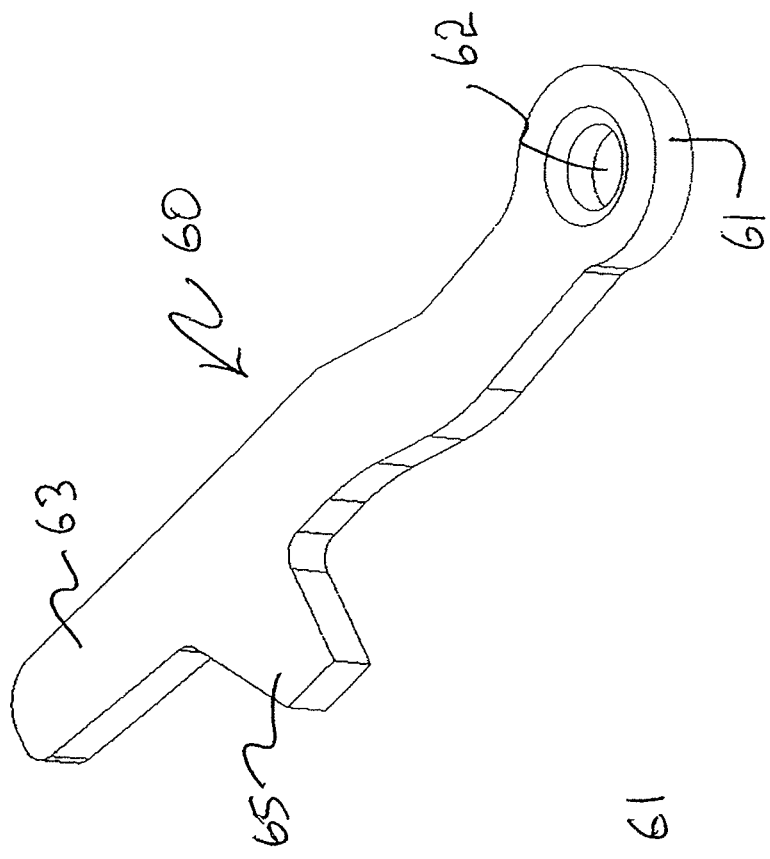
FIG. 49 shows a bottom perspective view of the locking member shown in FIG. 48.
Figure 48:
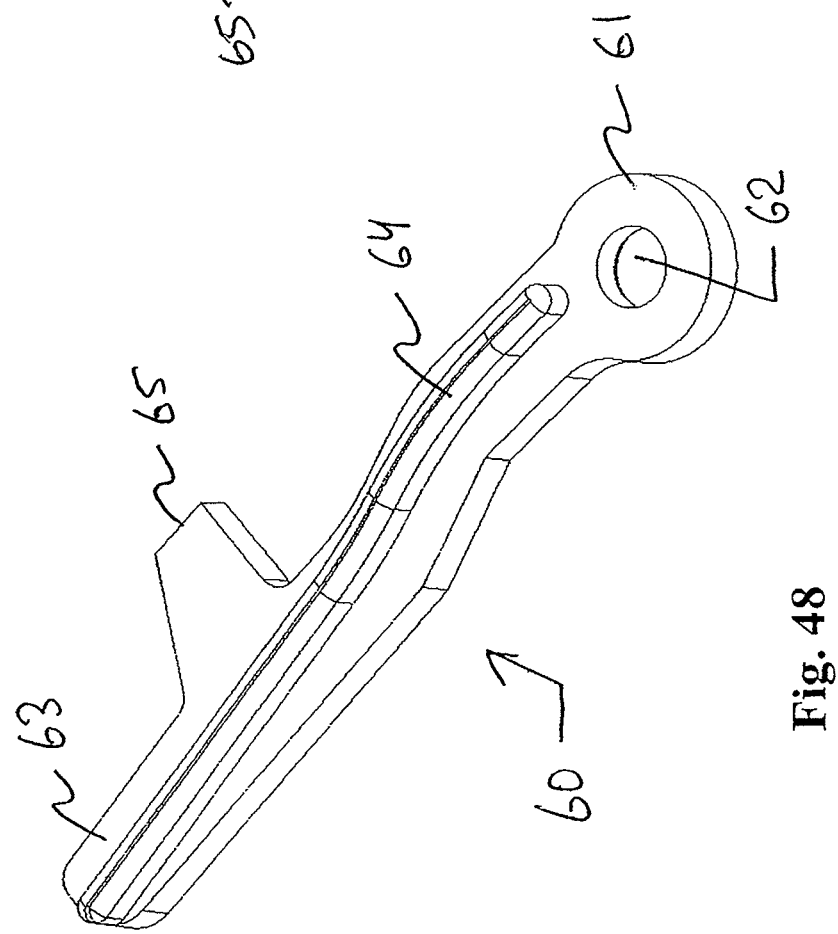
FIG. 48 shows a top perspective view of the locking member used in the lancet device shown in FIG. 1.

FIGS. 10-12 show various aspects of a lancet holding member lock system which is activated by the lancet ejection system. As is evident from FIG. 11, a lock member 60 has a rear mounting end 61 whose opening movably engages with a projection 10B10 of the body 10. This mounting allows the lock member 60 to pivot or partially rotate about the projection 10B10. The lock 60 is able to pivot while sliding over or against a support surface formed by a series of projections 10B11 (see FIG. 11). When the button portion of the ejector 50 is slid forward from an original position shown in FIG. 8 to an ejection position shown in FIG. 9, a portion 56 of the ejector 50 having a recess 57 slidably engages with a camming projection 64 and this engagement regulates the pivoting movement of the lock 60. The locking portion 65 is thus cause to move into and out of locking engagement with the lancet holding member 70. When the button portion of the ejector 50 is slid forward from an original position shown in FIGS. 8 and 12 to an ejection position shown in FIGS. 9 and 10, the locking portion 65 of the lock 60 is pivoted to a locking position such that the portion 65 obstructs movement of a projection 78 of the holding member 70. Thus, when the ejector 50 contacts a rear end of the installed lancet L and the lancet L is thus caused to moved out of engagement with the lancet holding member 70 as shown in FIG. 9, the holder 70 is prevented from also moving forward by the lock 60. The action or activation of the lancet ejection system LES thus automatically activates the lancet holding member lock system. Moreover, when the button portion of the lancet ejector 50 is released, it is automatically caused to move back to the position shown in FIGS. 8 and 12 by axial expansion of a spring S3. The spring S3 is axially compressed by a projecting portion 54 of the ejector 50 when it is slid forward to eject a lancet L. The movement of the ejector 50 back to an original position via the spring S3 also automatically results in the lock 60 being caused to move or pivot back to the unlocked position shown in FIGS. 8 and 12. Additional details of the lock member 60 are shown in FIGS. 48 and 49 which show the mounting portion 61, mounting opening 62, an opposite or forward end 63, camming projection 64, and locking portion or projection 65.

Figure 34:
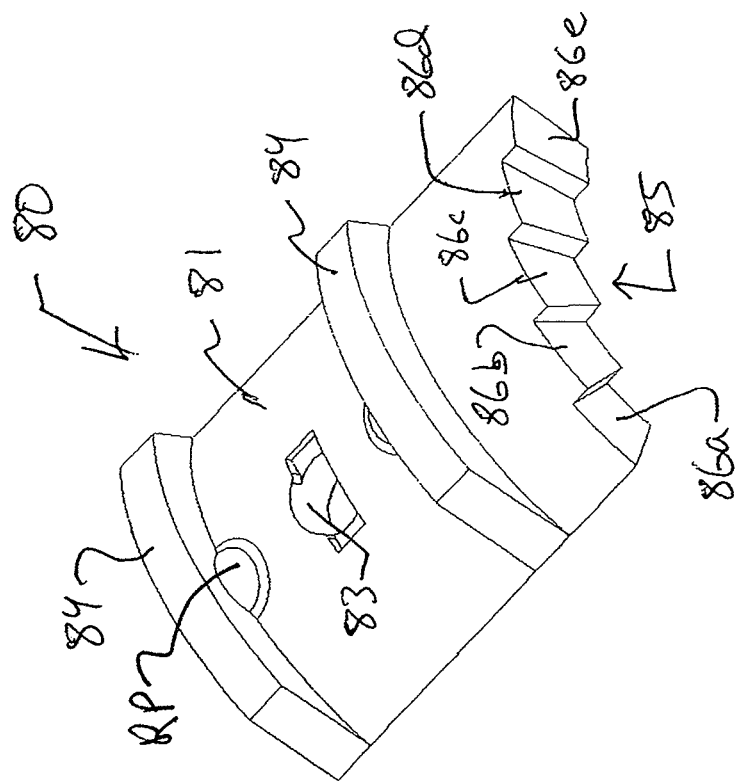
FIGS. 34 and 35 show perspective front and back side views of the depth adjustment member used in the embodiment of FIG. 1.
Figure 35:
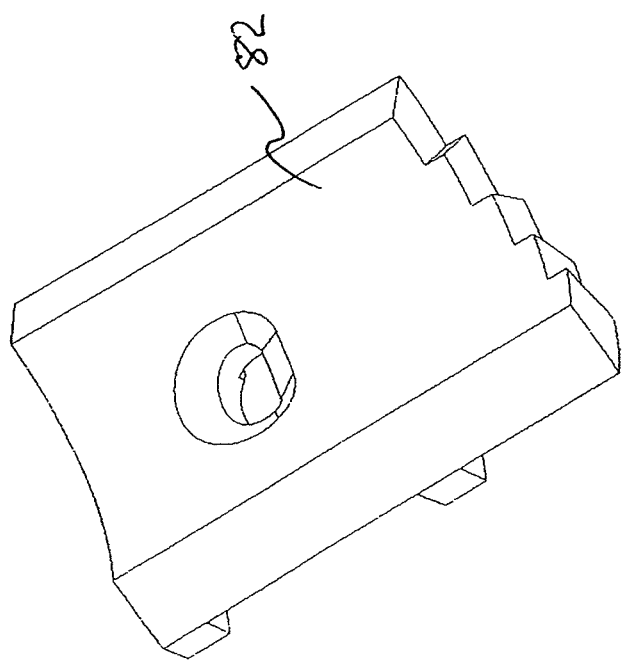

FIGS. 13-15 show various aspects of a depth adjustment system which is utilized on the lancet device LD. As is evident from FIGS. 13-15, a depth adjustment system has two main components. These are a slide or selector button 90 and a depth adjustment member 80. The button 90, which is shown in detail in FIGS. 36 and 37, has a main curved body 91 which can slide within a groove formed in the body 10. A friction surface 92 includes projections and recesses that prevent slipping between a user's finger and the body 91. A projection 93 is designed to extend through wall of the body 10 and engage with an opening 83 of the depth adjustment member 80. A position indicator 94 allows a user to determine which depth of penetration position is currently set on the lancet device LB. When a user moves the button 90 to a desired depth of penetration position, the depth adjustment member 80 is also moved. Each depth setting portion corresponds to one of the surfaces 86a-86e being positioned into alignment with a stop projection 74 of the lancet holding member 70. When the lancet holding member 70 is caused to move to a puncturing position upon triggering of the lancet device LD, the projection 74 will contact one of the surfaces 86a-86e and this contact prevents or limits depth of penetration. As should be apparent from FIGS. 13-15, when the lancet holding member 70 is caused to move to a puncturing position (see FIG. 14) from a trigger set position upon triggering of the lancet device LD, and the projection 74 contacts the surface 86a, this contact prevents or limits depth of penetration to a maximum or greatest penetration depth. However, when the lancet holding member 70 is caused to move to a puncturing position upon triggering of the lancet device LD, and the projection 74 contacts the surface 86e, this contact prevents or limits depth of penetration to a minimum or least penetration depth. A depth of penetration setting position that is between these two positions is shown in FIG. 1. To releasably retain the member 80 is a particular depth setting position, the member 80 has a series of partially rounded pairs of projections RP (see FIG. 15) which engage comparably sized retaining recesses RR of the body 10 (see FIG. 22). Additional details of the member 80 are shown in FIGS. 34 and 35 which show a main body portion 81, a curved inside surface 82, and curved guide projections 84.

Figure 16:
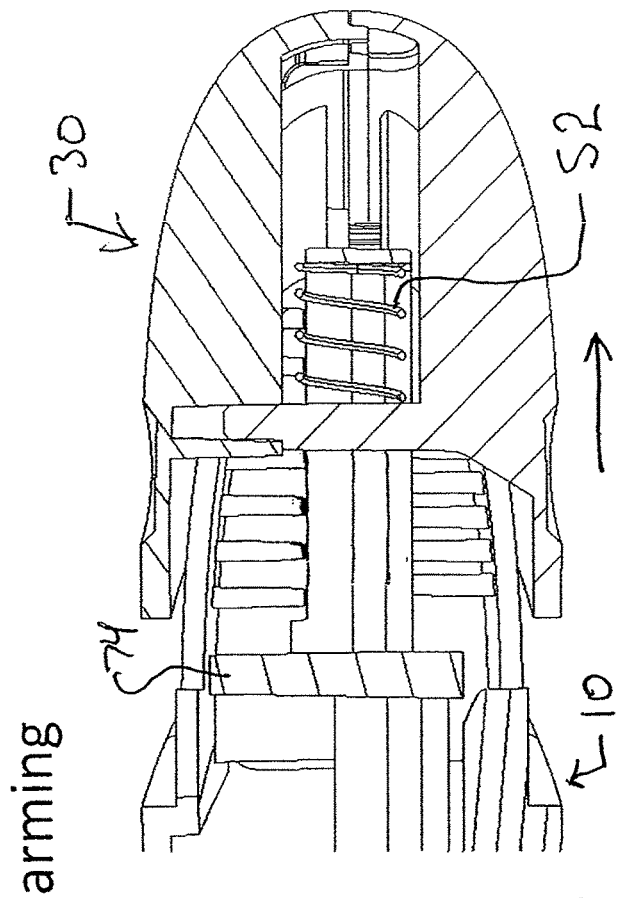
FIG. 16 shows an enlarged cross-section view of a rear portion of the lancet device of FIG. 3 and illustrates how the user can grip the back cap.
Figure 17:
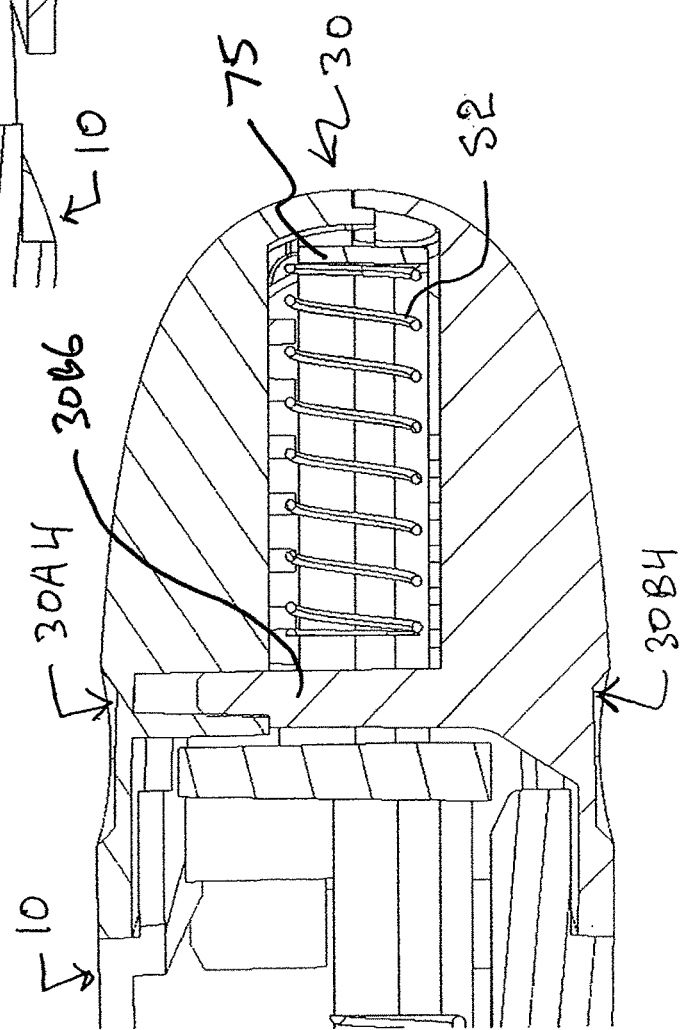
FIG. 17 shows the enlarged cross-section view of FIG. 16 and illustrates how the user can move the back cap to a trigger-set position so as to place the lancet device in the armed position of FIGS. 3 and 16.
Figure 28:
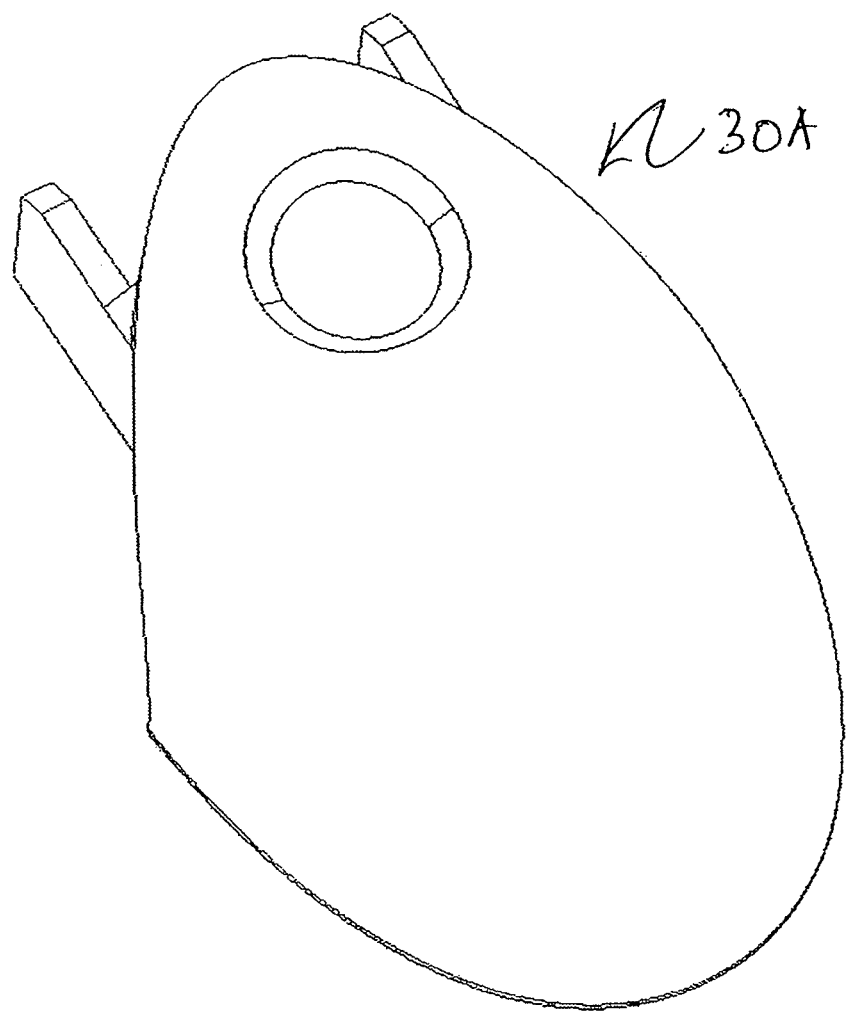
FIG. 28 shows a perspective rear side view of an upper portion of the back cap used in the lancet device shown in FIG. 1.
Figures 29, 30:
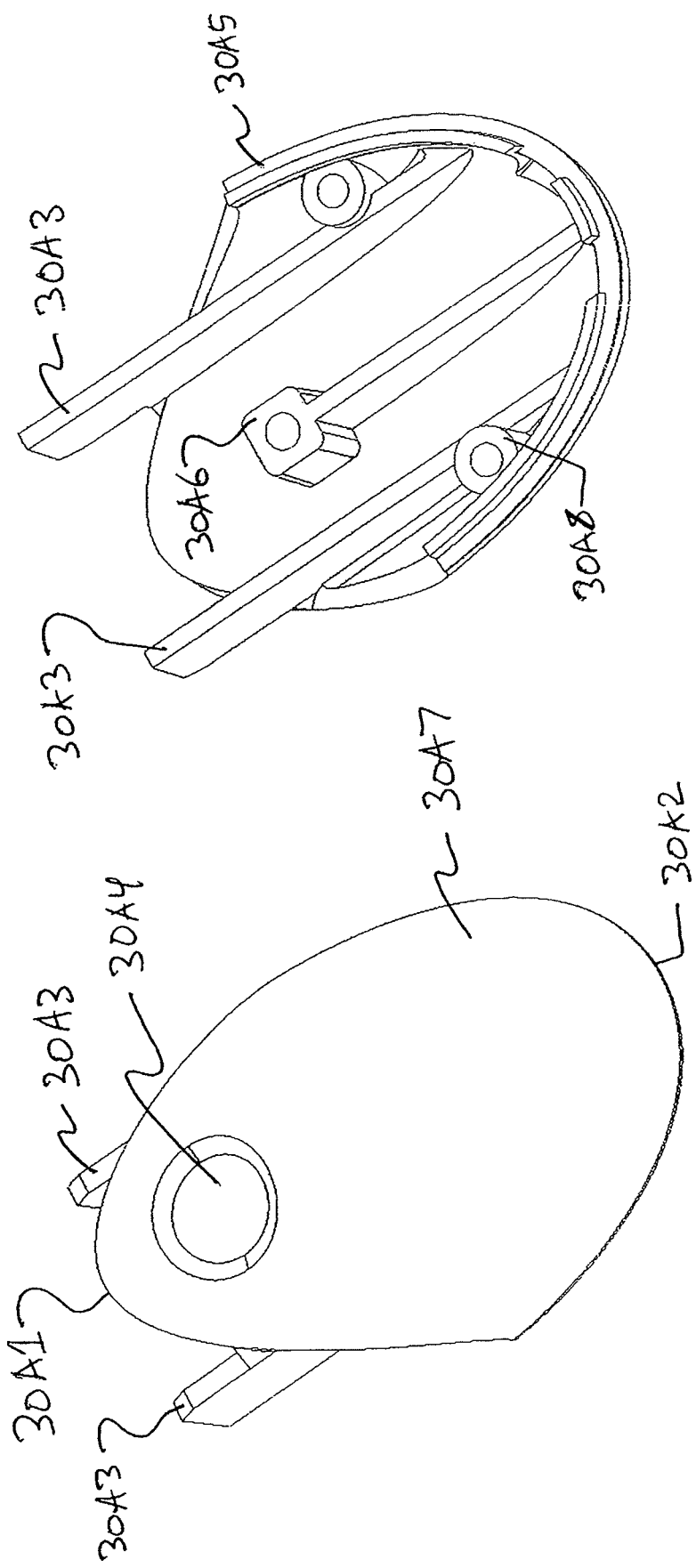
FIG. 29 shows an enlarged perspective rear side view of an upper portion of the back cap used in the lancet device shown in FIG. 1.
FIG. 30 shows a perspective inside view of the upper portion of the back cap shown in FIG. 29.
Figure 31:
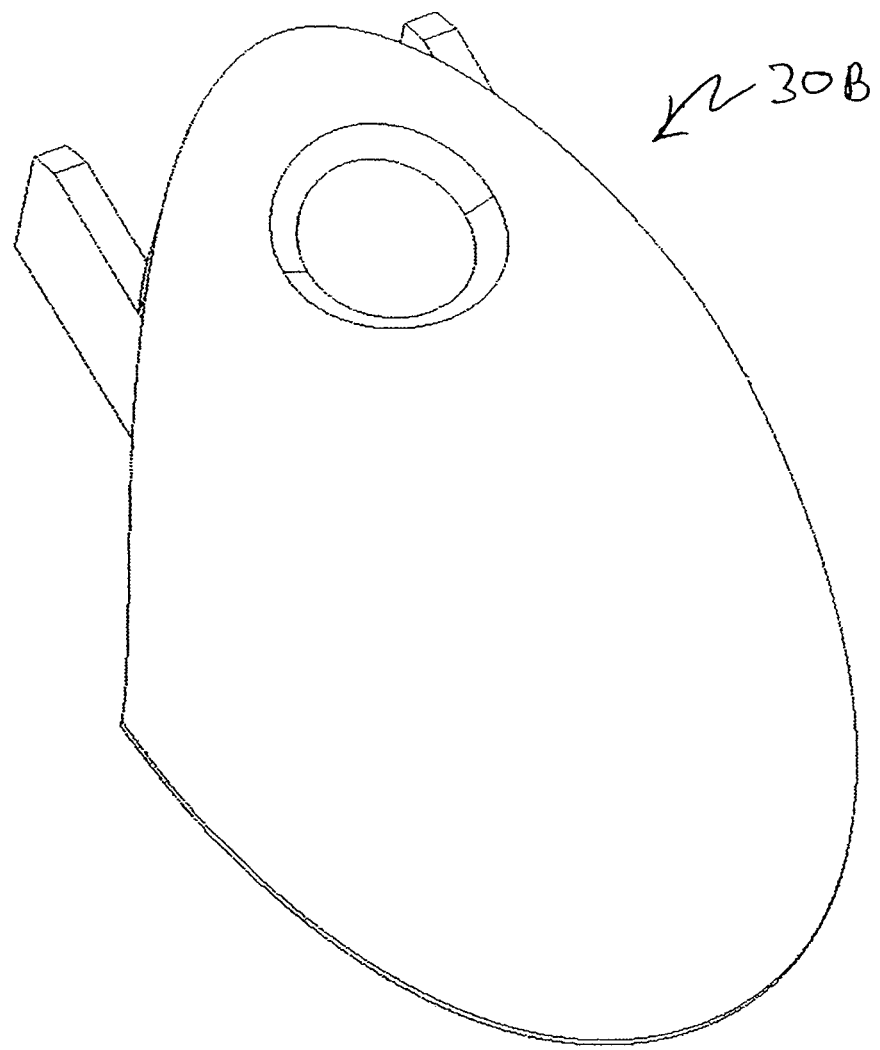
FIG. 31 shows a perspective rear side view of a lower portion of the back cap used in the lancet device shown in FIG. 1.
Figures 32, 33:
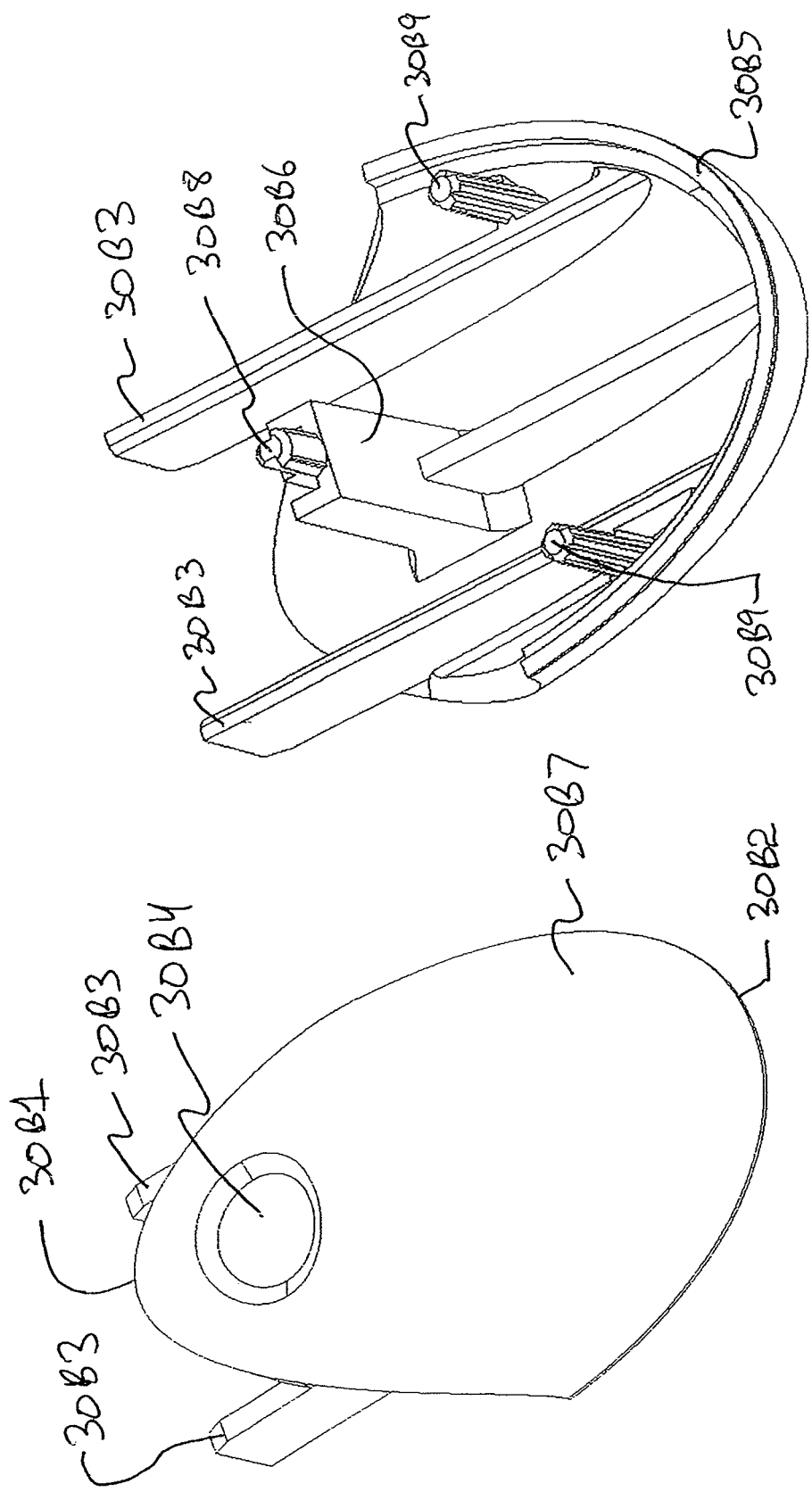
FIG. 32 shows an enlarged perspective rear side view of a lower portion of the back cap used in the lancet device shown in FIG. 1.
FIG. 33 shows a perspective inside view of the lower portion of the back cap shown in FIG. 32.

FIGS. 16 and 17 show various aspects of a cocking system which is utilized on the lancet device LD. As is evident from FIG. 16, a cocking member or back cap 30 is biased toward an original position shown in FIG. 16 via a spring S2. This occurs as a result of the front end of the spring S3 contacting or abutting the projection 30B6 (see also FIG. 33). The projection 30B6 passes into and through the slot 76b and the spring receiving space 76a (see FIGS. 43 and 44) of the holding member 70. The slightly compressed state of the spring S2 ensures that the curved edges 30A10 and 30B1 contact or abut comparably shaped surfaces or shoulder edges of the body 10. When the user desired to place the lancet device LD in a cocking or arming position, the user will grip the back cap 30 with two fingers and pull back on the back cap 30 relative to the body 10 in the direction shown by arrow in FIG. 17. This compresses the spring S2 which in turn causes the lancet holding member 70 to be moved away from the front end of the lancet device LD. During this movement, the stop projection 74 moves back away from one of the stop surfaces 86a-86e that is in alignment therewith. During this movement, the deflectable retaining projection 72 will become releasably retained or engaged with the retaining shoulder RS as described above with reference to FIG. 3. When the use then releases the back cap 30, it will be caused to automatically move back to the position shown in FIG. 16 by axial expansion of the spring S2. Additional details of the back cap 30 are shown in FIGS. 28-33 which show the back cap 30 having a two piece construction which facilitates assembly of the lancet device LD. A first piece is shown in FIGS. 28-30 and includes a curved front edge 30A1, a curved back edge 30A2, guide projections 30A3 which slidably engage with surfaces 10A25 and 10B25 of the body 10, a gripping indentation 30A4, a perimeter edge 30A5, a projection 30A6, and a curved shell exterior 30A7. A second piece is shown in FIGS. 31-33 and includes a curved front edge 30B1, a curved back edge 30B2, guide projections 30B3 which slidably engage with surfaces 10A25 and 10B25 of the body 10, a gripping indentation 30B4, a perimeter edge 30B5, a projection 30B6, and a curved shell exterior 30B7. In addition, a securing and retaining projection 30B8 is configured to extend into the opening formed in the projection 30A6 and two securing and retaining projection 30B9 are configured to extend into the openings formed in the projections 30A8.

Figure 18:
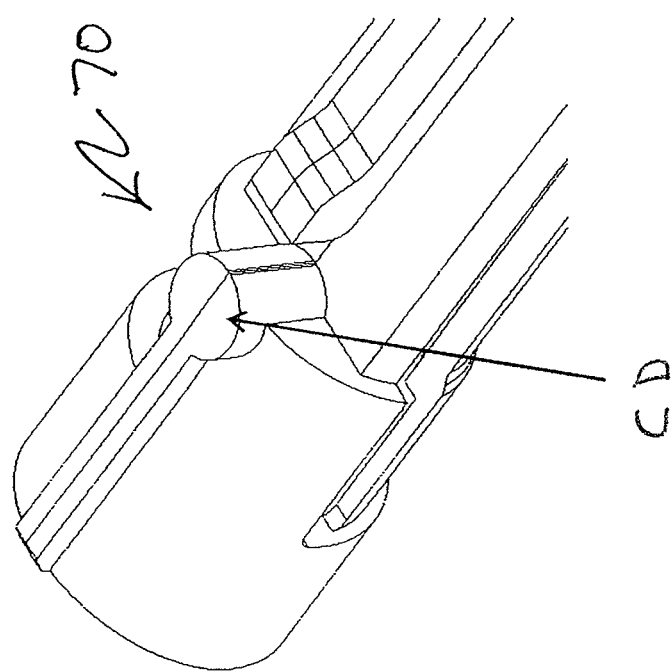
FIGS. 18 and 19 show a front portion of the lancet device and holding member and shows how a user can see a visible indicator of when the lancet device is in an armed position.
Figure 19:
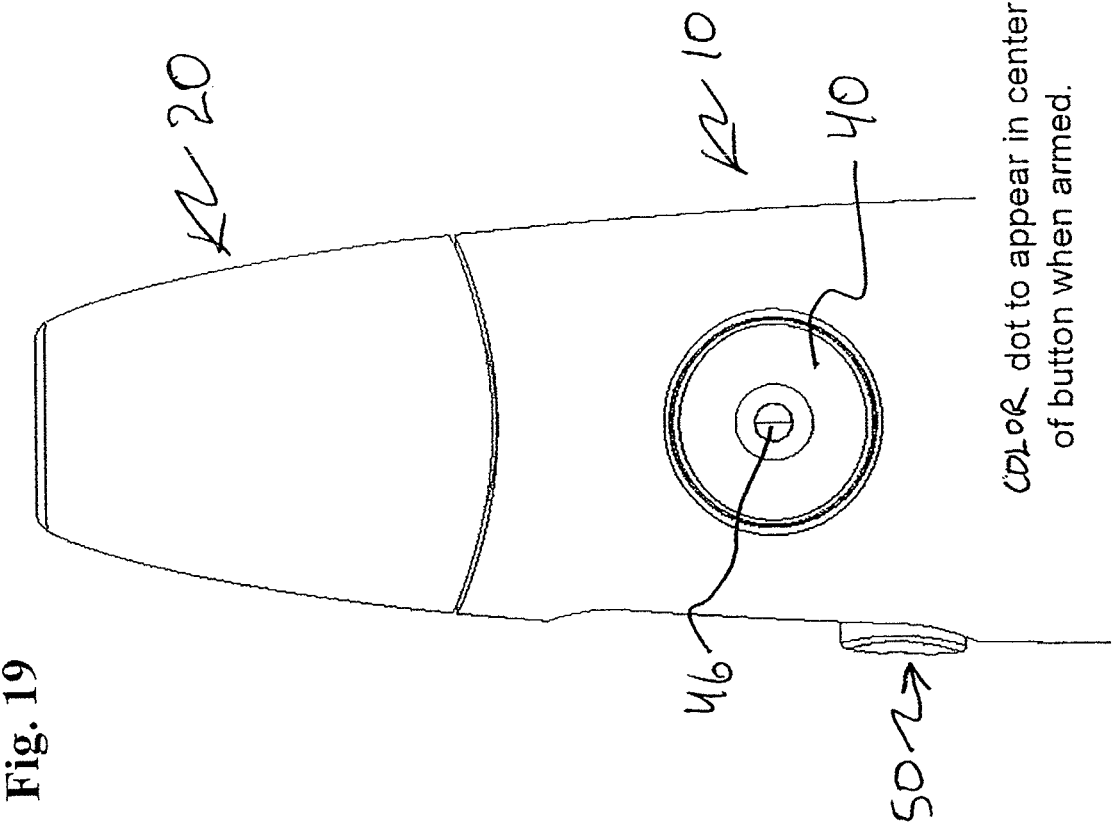
Figure 39:
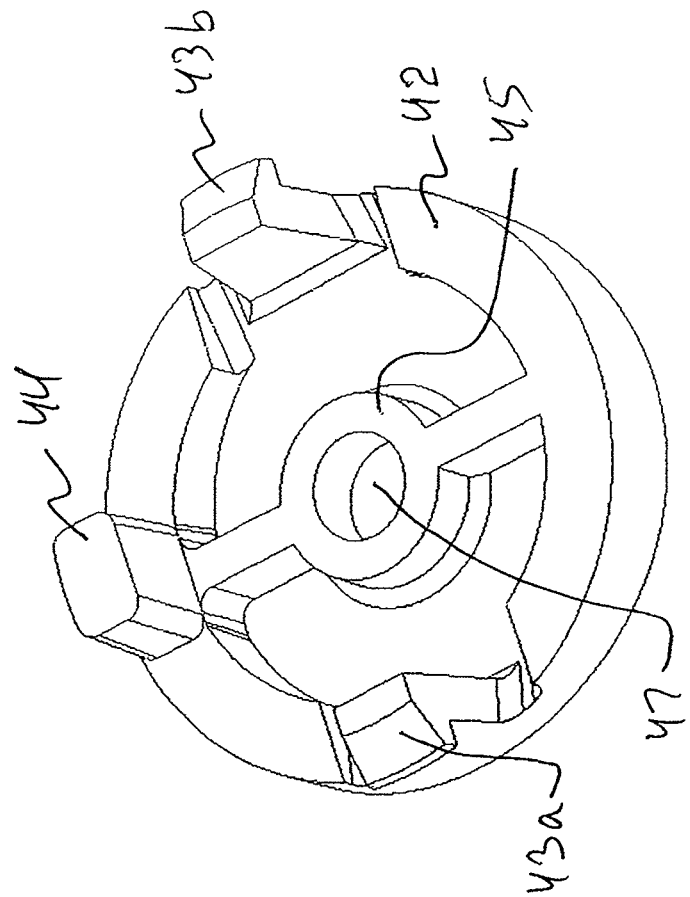
FIGS. 38 and 39 show perspective top and bottom views of the trigger used on the lancet device of FIG. 1.
Figure 38:
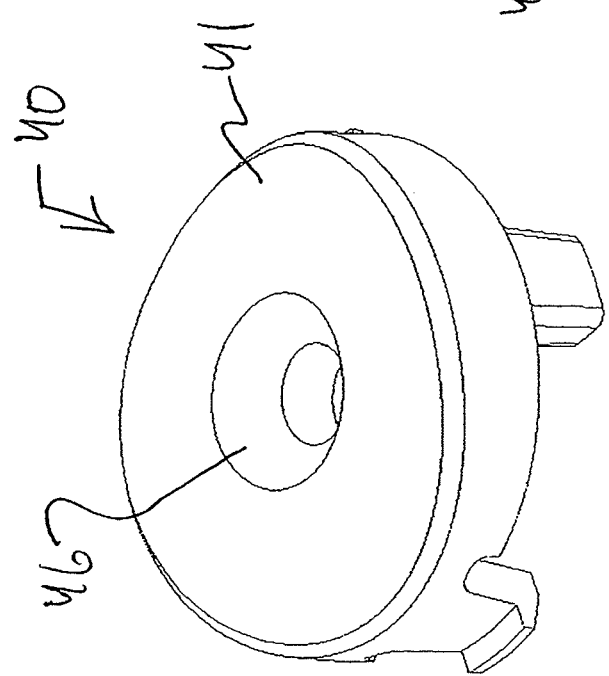
Figure 40:
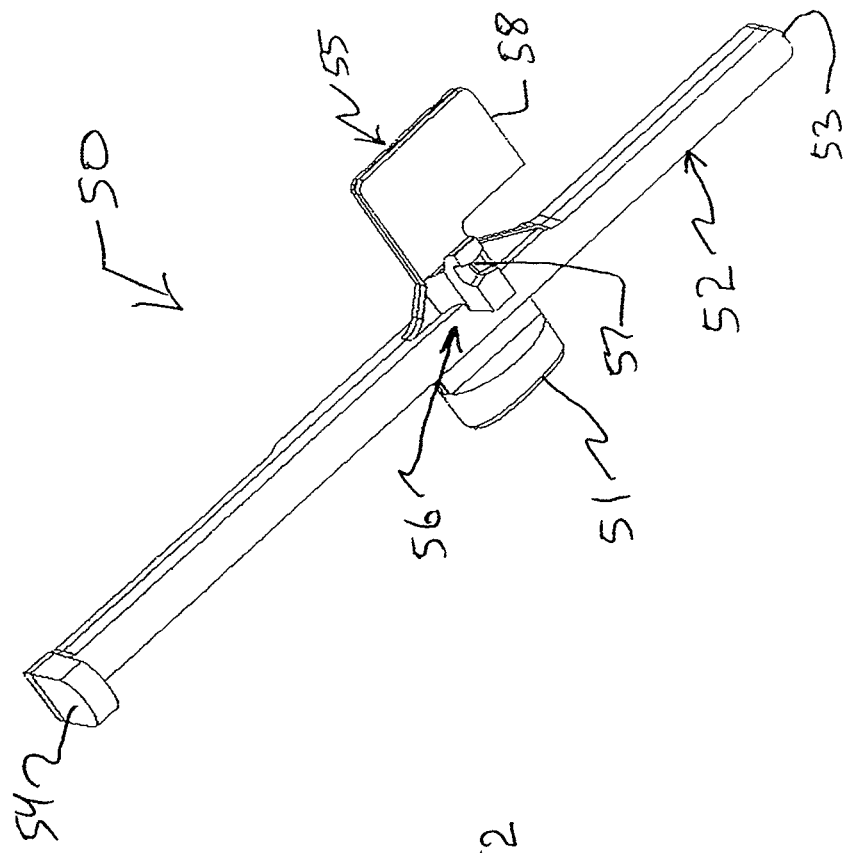
FIGS. 40 and 41 show perspective top and bottom views of the lancet ejection member used on the lancet device of FIG. 1.

FIGS. 18 and 19 show various aspects of a trigger system which is utilized on the lancet device LD. As is evident from FIG. 19, a trigger 40 is arranged on the body 10 at a location that is adjacent the lancet ejector 50 such that a central axis of the trigger 40 is generally perpendicular to a center axis of the button portion of the ejector 50, and also the movement direction of the ejector 50. Moreover, like the ejector 50, the trigger 40 is located closer to a front end of the lancet device LD than to a rear end. The trigger 40 also utilizes a central window area 46 which can be an opening or a transparent or translucent section. With such an arrangement, when a portion or projection of the lancet holding member 70, having a distinct color dot or spot such as, e.g., a red circular dot CD, is in alignment with the area 46, it provides a visual indicator to a user. In the non-limiting embodiment described herein, this visual indicator informs the user that the lancet device LD is in a trigger-set or armed position. When this is not the case, a user will know that the device LD is not armed and that he/she can safely handle the device LD without the risk of accidental triggering. Additional details of the trigger 40 are shown in FIGS. 38 and 39 which show a main trigger button body 41, a bottom peripheral edge 42, oppositely arranged retaining projections 43a and 43b, a triggering projection 44 which causes deflection of the deflectable projection 72 during triggering, a central projection 45, and a central indented area 46 having a central window or viewing opening 47.

FIGS. 20-25 show various aspects of a body 10 is utilized on the lancet device LD. As is evident from FIGS. 20 and 23, the body 10 is a two piece body that includes body portion 10A and body portion 10B—which can each be made as one-piece integrally formed members.

Figure 20:
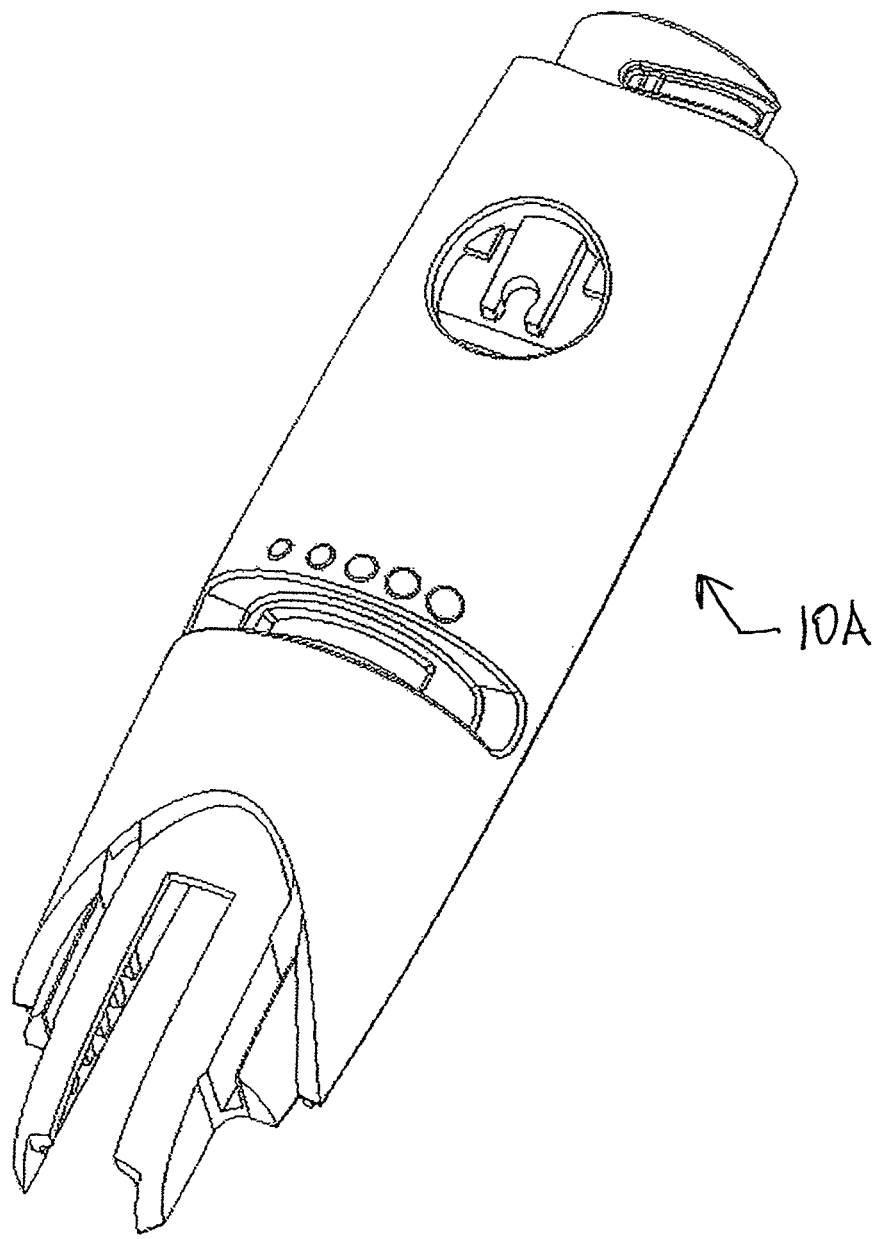
FIG. 20 shows a perspective top side view of the upper or right-side housing part used in the two-piece housing of the lancet device shown in FIG. 1.

As can be seen in FIGS. 20-22, the body portion 10A includes a semi-circular front end 10A1, a rear forked end 10A2, a semi-cylindrical shoulder or front cap mounting portion 10A3, an inner semi-cylindrical surface 10A4, a main body portion 10A5, generally centrally located connecting projection receiving openings 10A6, rear connecting projection receiving openings 10A7, front connecting projection receiving openings 10A8, a trigger mounting opening 10A10, a trigger leaf spring 10A11, a depth adjuster guide groove 10A12, and an ejector receiving opening 10A13 extending from a rear end 10A14 to a front end 10A15 thereof. The body portion 10A also includes a series of projections 10A16, rear planar support surfaces 10A19, reinforcing projection 10A20, reinforcing projection 10A21, a rear open area 10A22, a back cap receiving recess 10A23, guide surfaces 10A25 extending to guide slots 10A25a. A partially helical groove G is arranged on the surface 10A3 and a retaining projection forming a retaining shoulder RS is arranged in an area of the trigger opening 10A10.

Figure 23:
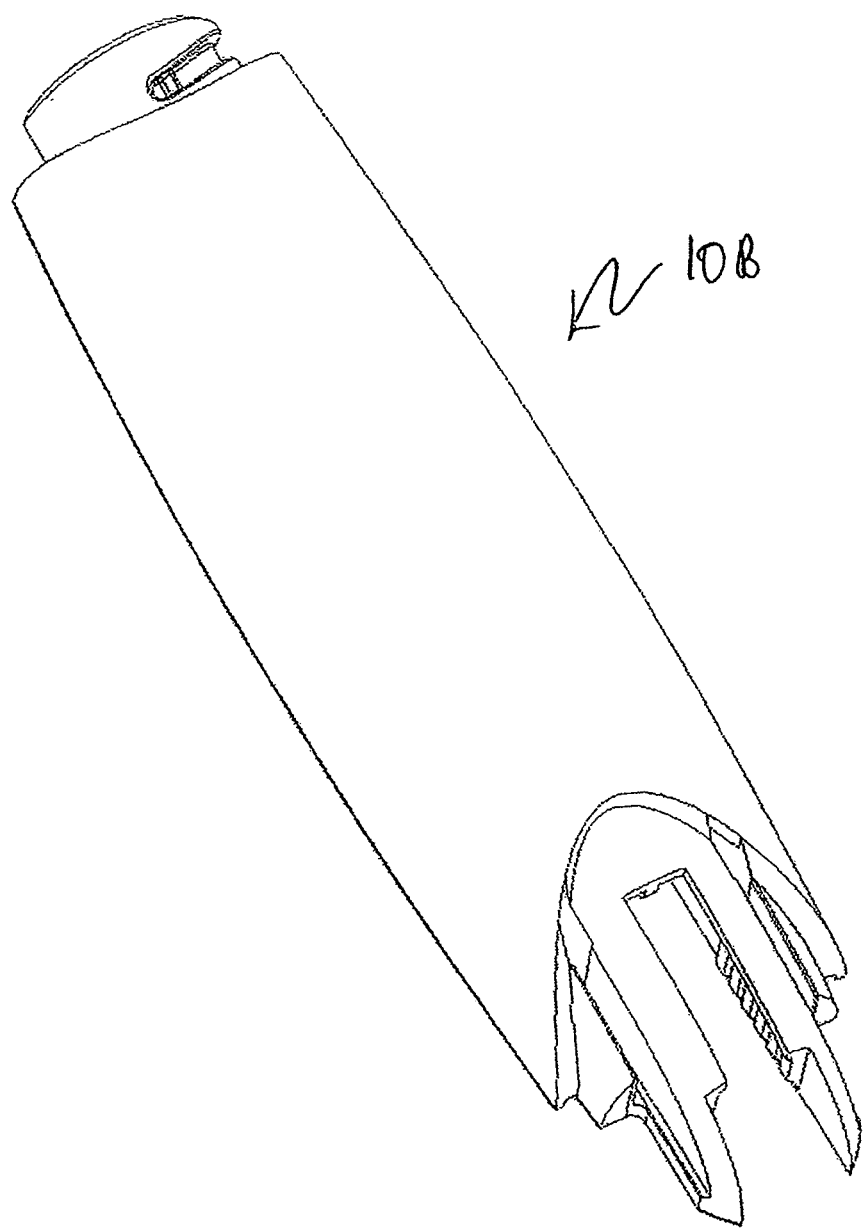
FIG. 23 shows a perspective bottom side view of the lower or left-side housing part used in the two-piece housing of the lancet device shown in FIG. 1.
Figure 25:
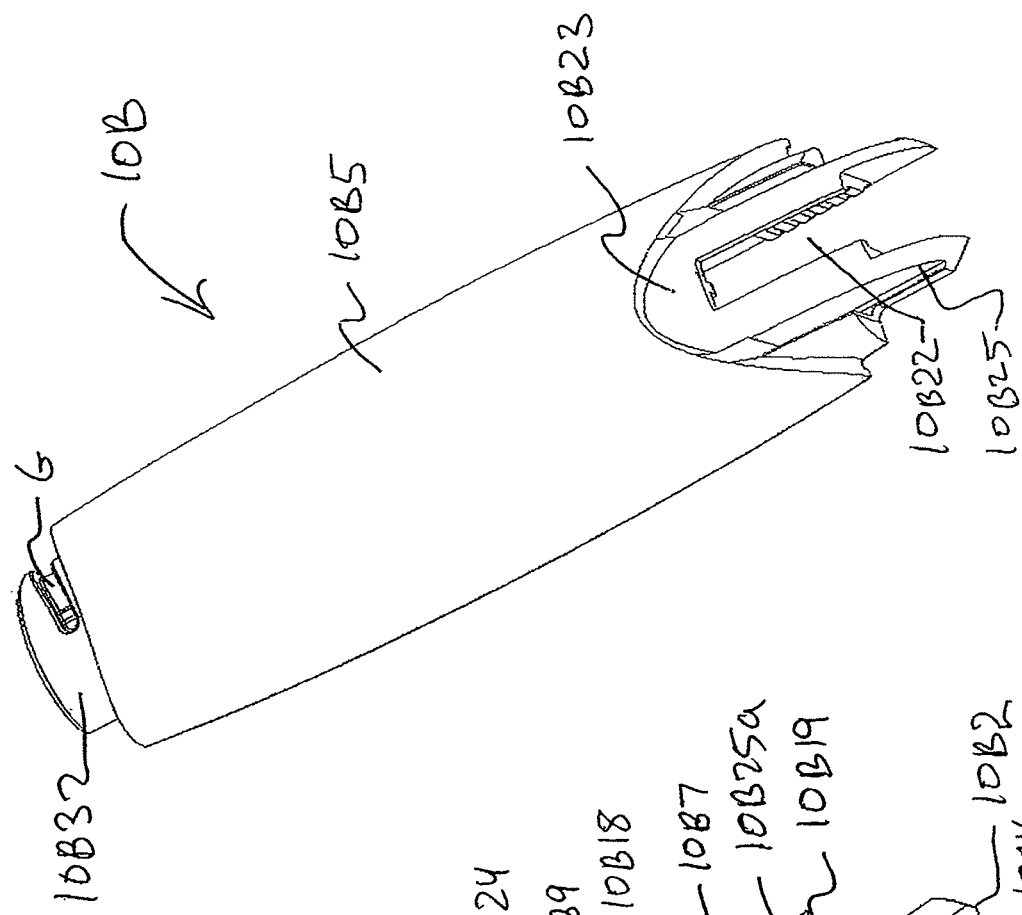
FIG. 25 shows a perspective outside view of the lower housing part shown in FIG. 23.
Figure 24:
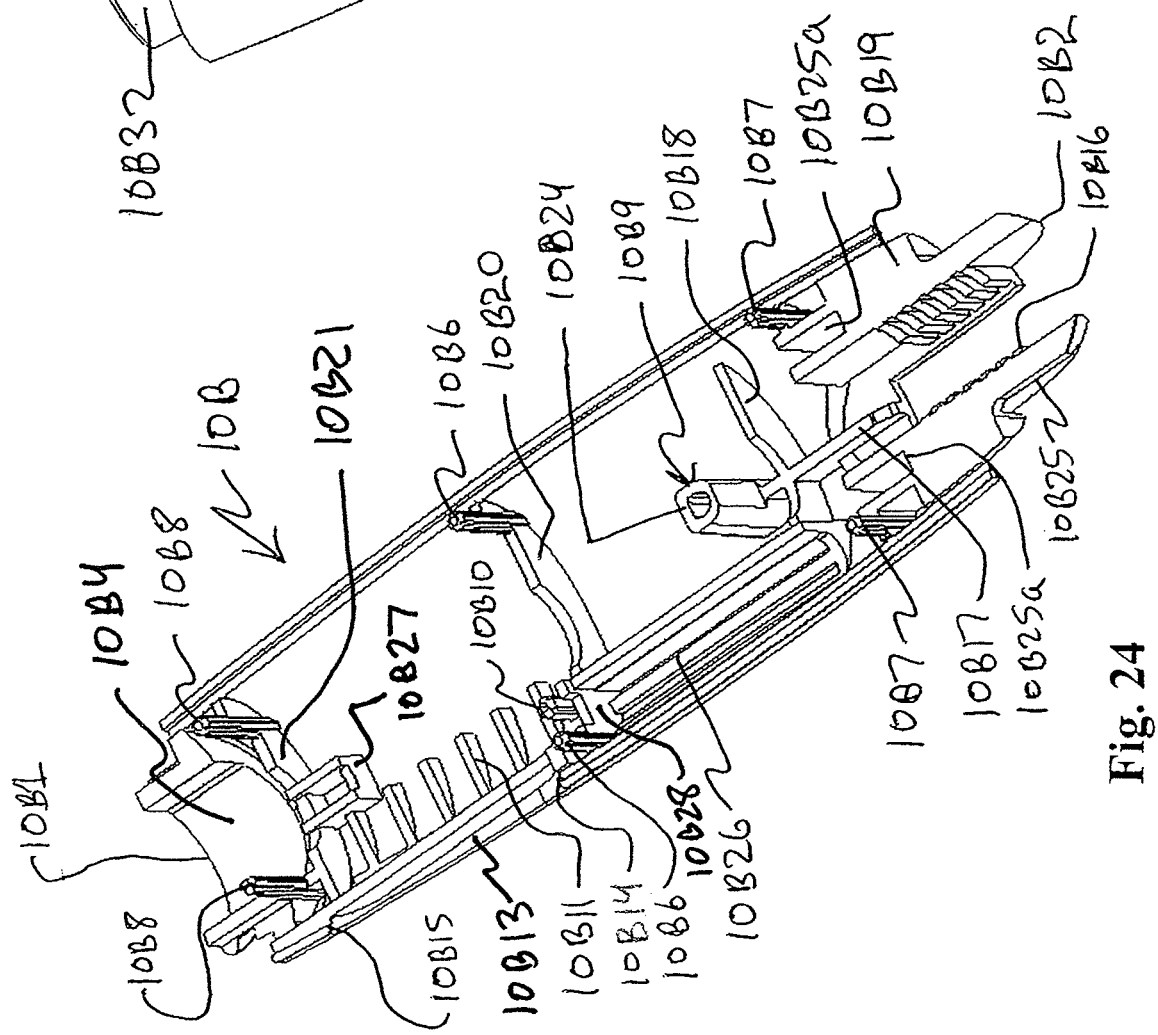
FIG. 24 shows a perspective inside view of the lower housing part shown in FIG. 23.

As can be seen in FIGS. 23-25, the body portion 10B includes a semi-circular front end 10B1, a rear forked end 10B2, a semi-cylindrical shoulder or front cap mounting portion 10B3, an inner semi-cylindrical surface 10B4, a main body portion 10B5, generally centrally located connecting projections 10B6 insertable into receiving openings 10A6, rear connecting projections 10B7 insertable into receiving openings 10A7, front connecting projections 10B8 insertable into receiving openings 10A8, a lock mounting projection 10810, plural support projections 10811, and an ejector receiving opening 10B13 extending from a rear end 10B14 to a front end 10B15 thereof. The body portion 10B also includes a series of projections 10B16, reinforcing projection 10B18, rear planar support surfaces 10B19, reinforcing projection 10B20, reinforcing projection 10B21, a rear open area 10B22, a back cap receiving recess 10B23, a main projection 10B9 having an upper surface 10B24, guide surfaces 10B25 extending to guide slots 10B25a. A spring receiving space or recess 10B26 is also utilized. A maximum movement limiting projection 10B27 is arranged on the body portion 10B and partially helical groove G is arranged on the surface 10B3.

FIGS. 42-44 show various aspects of a lancet holding member 70 which is utilized on the lancet device LD. As is evident from FIGS. 43 and 44, the holder 70 can utilize a one-piece body 71 having a central semi-cylindrical section 71c, a lancet receiving front end 71a and a rear end 71b. The holder 70 also includes a deflectable projection 72, a visual indicator projection 73, a separating wall projection 74, a rear wall 75. A spring receiving space is arranged within walls or surfaces 76a and 76c. A through slot 76a is sized to receive the projection 3086. Another spring receiving space is arranged within side surfaces 77a and 77c. A through slot 77a is sized to receive the projection 1089. The holder 70 additionally also includes a projection 78 and a side slot 79 which are utilized as part of the lancet ejection system and the lancet holder lock system.

Figure 47:
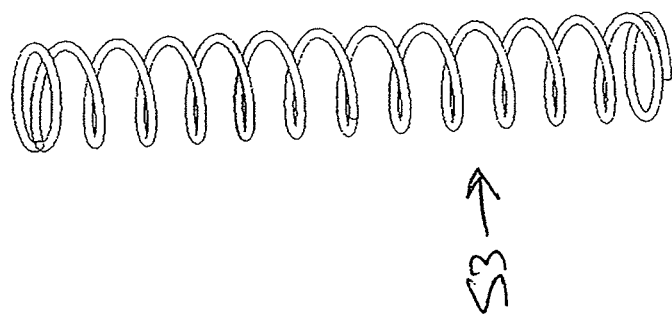
FIG. 47 shows a perspective side view of the spring used to bias the lancet ejection system of the lancet device shown in FIG. 1.
Figure 45:
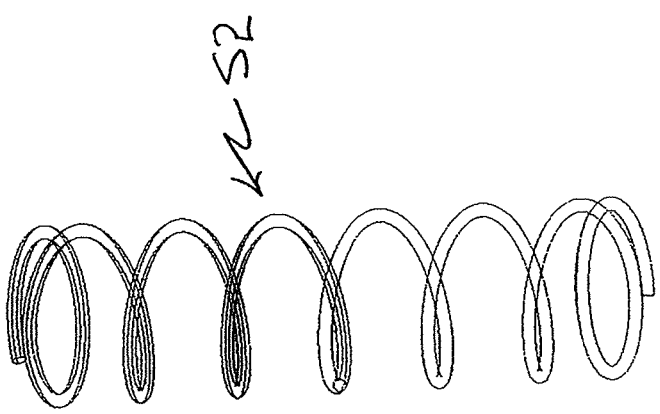
FIG. 45 shows a perspective side view of the lancet holding member/back cap return spring used on the lancet device of FIG. 1.
Figure 46:
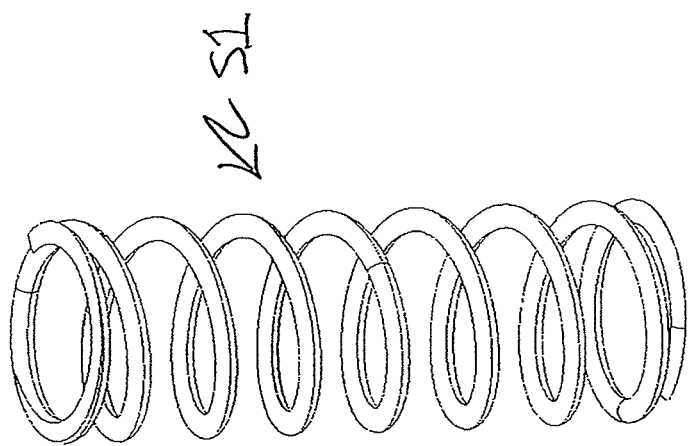
FIG. 46 shows a perspective side view of the drive spring which causes the lancet holding member to move to the puncturing position of the lancet device shown in FIG. 1.

FIGS. 45-47 show three main springs which are utilized on the lancet device LD. As is evident from FIG. 45, a second or return spring S2 is utilized and functions to return the lancet holding member 70 to an original position after triggering and after the contact between the projection 74 and one of the stop surfaces 86a-86e. The spring S2 is disposed in the space above the slot 76b. A rear end of the spring S2 contacts wall 75 while a front end contacts the projection 30B6. See FIG. 16. The spring S2 also functions to cause or bias the back cap 30 to more back to the position shown in FIG. 16 when released from the arming or cocking position shown in FIG. 17. As Is evident from FIG. 46, a first, main or drive spring Si is utilized and functions to cause the lancet holding member 70 to move to a puncturing position after triggering and has sufficient power to cause contact between the projection 74 and one of the stop surfaces 86a-86e. The spring Si is disposed in the space above the slot 77b. A rear end of the spring Si contacts projection 10B9 while a front end contacts the surface or wall 77c. See FIG. 13. As is evident from FIG. 47, a third or eject spring S3 is utilized and functions to cause the lancet ejection system LES and the lock member 60 to assume an original position shown in FIG. 8. The spring S3 is disposed in the space 10B26 and is compressed by movement of the ejector 50 to the position shown in FIG. 9. A rear end of the spring S3 contacts projection 54 while a front end contacts the surface or wall 10B28.

Figure 50:
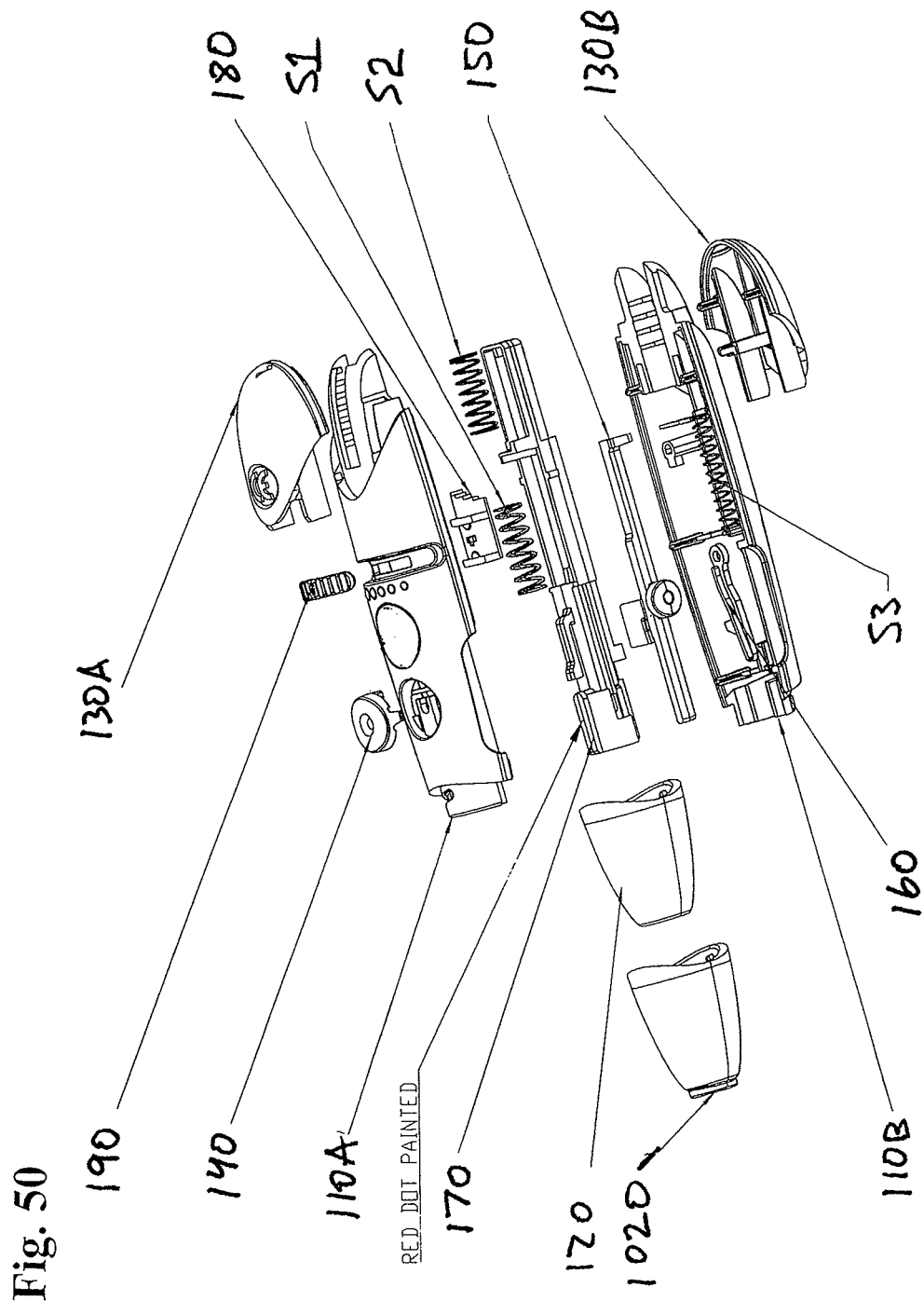
FIG. 50 shows an exploded view of another embodiment of a lancet device.
Figure 51:
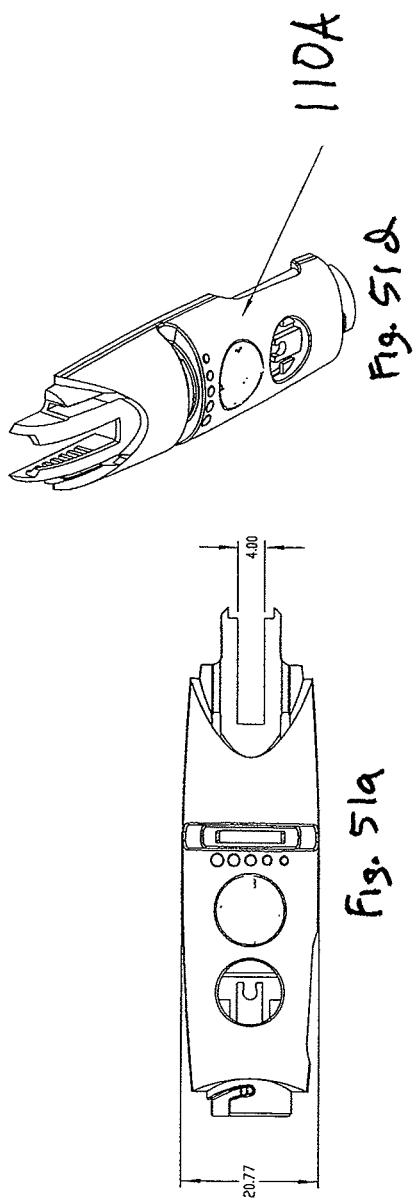
FIGS. 51 and/or 51a-51e show various view of a non-limiting commercial embodiment of an upper body portion having certain identified dimensions in millimeters and used on the lancet device of FIG. 50.
Figure 60:
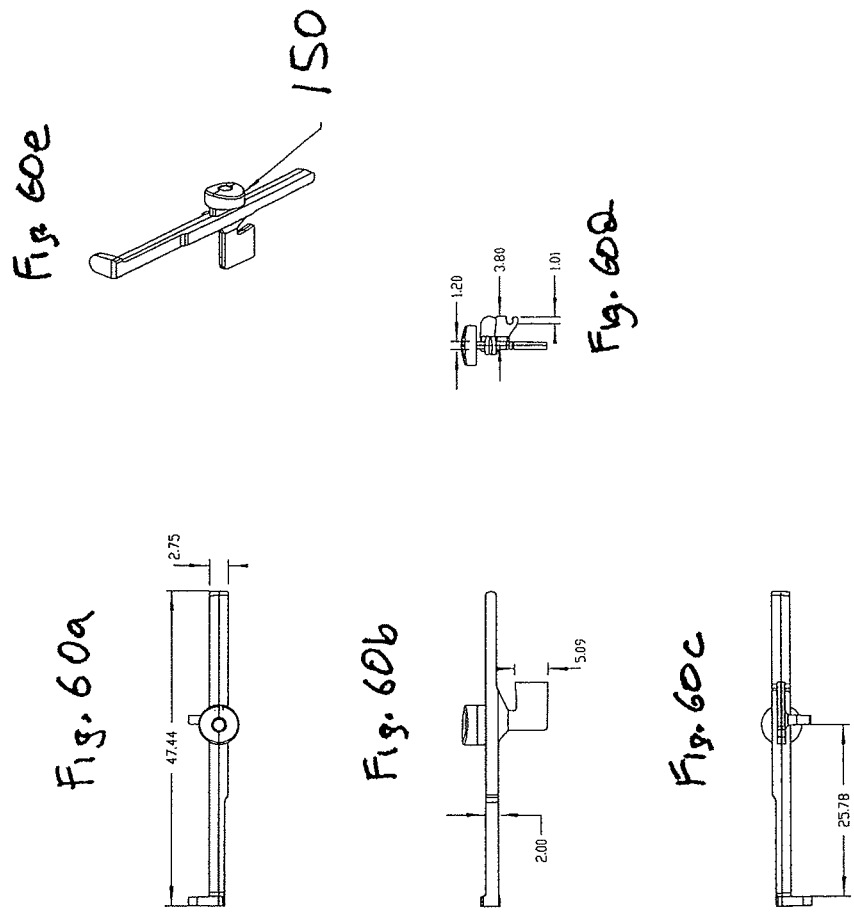
FIGS. 60 and/or 60a-60e show various view of a non-limiting commercial embodiment of a lancet ejector having certain identified dimensions in millimeters and used on the lancet device of FIG. 50.

FIGS. 50-65 show a non-limiting commercial embodiment of a lancet device. The lancet device includes comparable and/or substantially similar components to that shown in FIGS. 1-49. However, certain dimensions in millimeters are exemplified. As such, comparable reference numbers are utilized but increased by 100. For example, trigger 40 in FIG. 1 is comparable and/or substantially similar to trigger 140 in FIG. 50. FIGS. 50-65 thus include the following similar or comparable components: a housing or body 110 made of parts 110A and 110B, one or more front caps 120 and 1020, a back cap 30 made of parts 130A and 130B a trigger 140, a lancet advance or ejection button or member 150, a locking member 160, a lancet holding member 170, a depth adjustment system utilizing members 180 and 190, and three springs Si, S2 and S3. The function and operation of this embodiment is similar to that described with reference to FIGS. 1-49, and is not further described herein.

One or more of the parts of the lancet device LD such as, e.g., the housing 10, 110 and front cap 20, 120 and 1020, can preferably made transparent and/or translucent so that a user will clearly be able to see internal components. The device can also utilize one or more features or modifications disclosed in US 2006/0173478 to SCHRAGA, the disclosure of which is hereby expressly incorporated by reference in its entirety.

All the parts of the lancet device LD, with the exception of the springs and needles (which can respectively be made of spring steel and stainless steel), may be made from plastic materials and can be formed using conventional injection molding techniques or other known manufacturing methods. Bay way of non-limiting example, all or most of the parts such as the housing, trigger, front and back caps, thumb wheel, advance button, slide plate, lancet engaging member, locking member can be made of ABS plastic with the exception of the springs (which can be stainless steel) and the lancet holding member which can be made of polyoxymethylene (Delrin plastic). However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A lancet device comprising:
  a. a housing;
  b. a removable front cap mounted to the housing;
  c. a lancet holding member extending along an axial length of the housing, the lancet holding member having a front end adapted to receive therein a removable lancet, a rear end and a stop projection between the front end and rear end;
  d. a trigger;
  e. an arming system comprising a grippable cocking member engaged with a rear end of the housing and the rear end of the lancet holding member, the arming system structured and arranged to place the lancet device in a trigger-set or armed position;

f. a depth adjustment system comprising:
  a slide that:
    i. is at least slidable about a portion of a circumference of the housing and partially rotatably mounted;
    ii. has an axis of rotation arranged substantially parallel to a center axis of the lancet holding member, and
    iii. is movable along a curved path between plural depth of penetration setting positions; and
  a depth adjustment member that:
    i. is engaged with the slide within the housing;
    ii. is movable by the slide between the plural depth of penetration setting positions along a curved path within the housing;
    iii. has an axis of rotation arranged substantially parallel to the center axis of the lancet holding member, and
    iv. has stop surfaces along a first end that correspond to the plural depth of penetration setting positions, where the stop surfaces engage with the stop projection to limit axial movement of the lancet holding member; and
g. an ejection system comprising an ejector having a portion extending outside a sidewall opening of the housing and a portion that engages with an end of the removable lancet in the lancet holding member; and being located closer to a front end of the housing than to a rear end of the housing, wherein the ejection system is structured and arranged to:
  i. prevent axial movement of the lancet holding member; and
  ii. remove or eject a lancet from the lancet holding member.

2. The lancet device of claim 1, wherein the sidewall opening is arranged on an area of the housing located between the trigger and a wall of the housing located opposite the trigger.

3. The lancet device of claim 2, wherein the ejector comprises a manually activated slide button extending outside the sidewall opening of the housing.

4. The lancet device of claim 3, wherein the slide comprises a selector button movable from outside the housing.

5. The lancet device of claim 4, wherein the selector button has a grip surface.

6. The lancet device of claim 4, wherein the selector button is movable relative to the hosing along a direction perpendicular to a longitudinal axis of the lancet device.

7. The lancet device of claim 1, wherein the slide is a one-piece member comprising indicia.

8. The lancet device of claim 1, further comprising a first spring configured to cause movement of the lancet holding member towards a puncturing position and a second spring configured to cause a back cap to move towards an initial position from a retracted position.

9. The lancet device of claim 1, further comprising a first spring configured to cause movement of the lancet holding member towards a puncturing position, a second spring configured to cause a back cap to move towards an initial position from a retracted position, and a third spring configured to cause a slide member of the ejection system to move towards an initial position from an extended position.

10. The lancet device of claim 1, wherein the slide comprises an arcuate-shaped member having two or more cam or stop surfaces.

11. The lancet device of claim 1, comprising indicia arranged on the housing.

12. The lancet device of claim 1, wherein the trigger is arranged on at least one of:
  a. a lateral side of the lancet device; or
  b. a side wall of the housing.

13. The lancet device of claim 1, wherein the ejection system is structured and arranged to prevent axial movement of the lancet holding member via a locking member.

* * * * *